United States Patent
Andreiko et al.

(10) Patent No.: US 9,345,553 B2
(45) Date of Patent: May 24, 2016

(54) METHOD, SYSTEM, AND COMPUTER PROGRAM PRODUCT TO PERFORM DIGITAL ORTHODONTICS AT ONE OR MORE SITES

(71) Applicant: Ormco Corporation, Orange, CA (US)

(72) Inventors: Craig A. Andreiko, Alta Loma, CA (US); David M. Sarver, Vestavia Hills, AL (US)

(73) Assignee: Ormco Corporation, Orange, CA (US)

( * ) Notice: Subject to any disclaimer, the term of this patent is extended or adjusted under 35 U.S.C. 154(b) by 686 days.

(21) Appl. No.: 13/665,663

(22) Filed: Oct. 31, 2012

(65) Prior Publication Data

US 2014/0122027 A1 May 1, 2014

(51) Int. Cl.
| | | |
|---|---|---|
| G06F 17/50 | (2006.01) |
| A61C 3/00 | (2006.01) |
| A61C 9/00 | (2006.01) |
| A61C 7/00 | (2006.01) |
| G01T 1/00 | (2006.01) |
| A61C 13/34 | (2006.01) |

(52) U.S. Cl.
CPC . *A61C 3/00* (2013.01); *A61C 7/002* (2013.01); *A61C 9/0006* (2013.01); *A61C 9/004* (2013.01); *A61C 13/34* (2013.01); *G01T 1/00* (2013.01)

(58) Field of Classification Search
CPC ........... A61C 7/002; G06T 1/00; G06T 17/00
See application file for complete search history.

(56) References Cited

U.S. PATENT DOCUMENTS

| | | | | |
|---|---|---|---|---|
| 5,368,478 A * | 11/1994 | Andreiko et al. | ............... | 433/24 |
| 5,431,562 A * | 7/1995 | Andreiko et al. | ............... | 433/24 |
| 5,447,432 A * | 9/1995 | Andreiko et al. | ............... | 433/24 |
| 5,548,698 A * | 8/1996 | Smith et al. | .................. | 345/660 |
| 5,552,995 A * | 9/1996 | Sebastian | ........................ | 700/97 |
| 5,862,260 A * | 1/1999 | Rhoads | ........................ | 382/232 |
| 6,089,868 A * | 7/2000 | Jordan et al. | .................. | 433/215 |
| 6,493,415 B1* | 12/2002 | Arai et al. | .......................... | 378/4 |
| 8,899,977 B2* | 12/2014 | Cao et al. | ........................ | 433/24 |
| 2004/0152036 A1* | 8/2004 | Abolfathi | ........................ | 433/24 |
| 2005/0170309 A1* | 8/2005 | Raby et al. | ........................ | 433/24 |
| 2006/0073436 A1* | 4/2006 | Raby et al. | ........................ | 433/24 |
| 2006/0105286 A1* | 5/2006 | Raby et al. | ........................ | 433/24 |
| 2006/0127854 A1* | 6/2006 | Wen | ............................. | 433/213 |

(Continued)

FOREIGN PATENT DOCUMENTS

| | | |
|---|---|---|
| WO | 2004/098378 | 11/2004 |
| WO | 2006/065955 | 6/2006 |

OTHER PUBLICATIONS

Response for EP Application No. 13190533.3-1658, dated Nov. 6, 2014, 9 pp. [20.01EP (EP SR)].

(Continued)

*Primary Examiner* — Ramesh Patel
(74) *Attorney, Agent, or Firm* — Wood, Herron & Evans, LLP

(57) ABSTRACT

A set of rules to design an orthodontic appliance for generating an aesthetic smile is maintained in a computational device, where the set of rules is associated with an application that executes in the computational device. At least one measured value is computed from one or more features extracted by processing dental information of a patient. The application generates a parameter to design an orthodontic appliance based on the at least one measured value and the set of rules for generating the aesthetic smile.

22 Claims, 31 Drawing Sheets

(56) References Cited

U.S. PATENT DOCUMENTS

| | | | |
|---|---|---|---|
| 2007/0168152 A1* | 7/2007 | Matov et al. | 702/155 |
| 2009/0017410 A1* | 1/2009 | Raby et al. | 433/2 |
| 2010/0129762 A1 | 5/2010 | Mason et al. | |
| 2010/0229413 A1* | 9/2010 | Polei | 33/514 |
| 2010/0244294 A1* | 9/2010 | Karim et al. | 264/18 |
| 2011/0267337 A1 | 11/2011 | Getto et al. | |
| 2014/0294273 A1* | 10/2014 | Jaisson | 382/131 |

OTHER PUBLICATIONS

Search Report for EP Application No. 13190533.3-1658, dated Jan. 27, 2014, 5 pp. [20.01EP (EP SR)].

* cited by examiner

METHOD, SYSTEM, AND COMPUTER PROGRAM PRODUCT TO PERFORM DIGITAL ORTHODONTICS AT ONE OR MORE SITES

BACKGROUND

1. Field

The disclosure relates to a method, system, and computer program product to perform digital orthodontics at one or more sites.

2. Background

Orthodontics is a specialty of dentistry that is concerned with improvement of the general appearance of a patient's teeth and also the correction of malocclusions, crookedness and other flaws of the teeth. Orthodontic braces are devices that are placed on a patient's teeth by a dental practitioner. Often, such orthodontic braces are periodically adjusted by the dental practitioner to help align and straighten the teeth. Treatment by the dental practitioner may help in repositioning the teeth to correct flaws and improve the general appearance of the patient.

The dental practitioner may take impressions and capture X-ray images of the teeth and the surrounding skeletal structure. The X-ray images may be generated via digital radiography in which a digital image capture device is used for recording the X-ray images, and subsequently the X-ray images are saved as digital files. The X-ray images may include panoramic X-rays and cephalometric X-rays. The panoramic X-rays may show the relative positions of the teeth over the upper jaw and the lower jaw. The cephalometric X-rays may show the skeletal relationships associated with the teeth in different views of the head. The cephalometric X-ray may also provide information about various angles and relationships associated with the teeth and the surrounding facial skeletal structure. Cephalometric analysis is the study of the dental and skeletal relationships in the head. Cephalometric software may used to help calculate the angles and measurements for cephalometric analysis from the digital cephalometric X-rays.

Cone beam computed tomography (CBCT) involves the use of a rotating CBCT scanner, combined with a digital computer, to obtain images of the teeth and surrounding bone structure, soft tissue, muscle, blood vessels, etc. CBCT may be used in a dental practitioner's office to generate cross sectional images of teeth and the surrounding bone structure, soft tissue, muscle, blood vessels, etc. During a CBCT scan, the CBCT scanner rotates around the patient's head and may obtain hundreds of distinct CBCT images. The scanning software collects and analyzes the CBCT images to generate three-dimensional anatomical data. The three-dimensional anatomical data can then be manipulated and visualized with specialized software to allow for cephalometric analysis of the CBCT images.

A dental practitioner may write a prescription based on an analysis of the impression of the teeth, the X-ray images, the CBCT images, etc. While performing the analysis the dental practitioner may use software for cephalometric analysis of the CBCT images, the panoramic X-rays, and the cephalometric X-rays.

The prescription written by the dental practitioner may be used to manufacture an orthodontic brace. In a traditional orthodontic brace, wires interact with brackets to move teeth to a desired position. Periodic adjustments are needed to the orthodontic brace for satisfactory completion of treatment. Other methods that use clear removable plastic aligners that level and align teeth may also be used by certain dental practitioners.

SUMMARY OF THE PREFERRED EMBODIMENTS

Provided are a method, system, and a computer program product, in which a computational device maintains a set of rules to design an orthodontic appliance for generating an aesthetic smile, where the set of rules is associated with an application that executes in the computational device. At least one measured value is computed from one or more features extracted by processing dental information of a patient. The application generates a parameter to design an orthodontic appliance based on the at least one measured value and the set of rules for generating the aesthetic smile.

In certain embodiments, a three-dimensional view of the aesthetic smile of the patient is generated based on simulating a treatment of the patient with the designed orthodontic appliance. The three-dimensional view of the aesthetic smile of the patient is transmitted.

In further embodiments, the three-dimensional view of the aesthetic smile of the patient is displayed to the patient.

In yet further embodiments, a tentative treatment plan based on the generated parameter is sent to design the orthodontic appliance. A sequence of images is sent, wherein the tentative treatment plan was generated based on the sequence of images. An approved treatment plan is received, in response to the sending of the tentative treatment plan and the sending of the sequence of images. A log file with timestamps corresponding the approved treatment plan is maintained.

In additional embodiments, the orthodontic appliance is designed, in response to receiving the approved treatment plan. The designed orthodontic appliance is sent to a custom orthodontic appliance production device.

In yet additional embodiments, the custom orthodontic appliance production device manufactures the designed orthodontic appliance. The manufactured custom orthodontic appliance is shipped.

In certain embodiments, the computational device includes code corresponding to the application. The application maintains the set of rules, wherein the set of rules include rules on at least aesthetics of smile. Anthropomorphic measurements computed from at least the dental information are maintained. At least the parameter to design the orthodontic appliance is generated, based on the maintained set of rules and the maintained anthropomorphic measurements.

In further embodiments, the computational device is maintained at a site controlled by a manufacturer of the orthodontic appliance, and a clinic site device is maintained at a site controlled by a dental practitioner.

In yet further embodiments, the dental information comprises at least one of photographic imagery, digital video imagery, intra-oral scan imagery, cone beam computed tomography imagery, X-ray imagery, magnetic resonance imagery, ultrasound imagery, and electron beam imagery, wherein the dental information includes images of soft tissue, hard tissue, and teeth of the patient.

In certain embodiments, the at least one measured value is the commissure width and at least one rule of the set of rules relates the commissure width to a dimension of the orthodontic appliance.

In additional embodiments, the generated parameter to design the orthodontic appliance is configured to allow the patient employing the orthodontic appliance on the teeth to achieve a smile in conformance with a selected aesthetics rule maintained in the set of rules.

In yet additional embodiments, the selected aesthetics rule provides an optimal smile to the patient in conformance with an optimization criterion based on which the selected aesthetics rules are maintained.

In certain embodiments, the computational device receives general case preferences from a dental practitioner during registration of the dental practitioner, wherein the general case preferences include at least one of appliance preferences, torque values, and end of treatment preferences.

In further embodiments, incremental imagery that includes modifications to already maintained dental information is sent, wherein the incremental imagery reduces an amount of data transmission.

In additional embodiments, the dental information includes a photograph taken at an eye level of the patient.

In yet additional embodiments, the application generates anthropomorphic measurements corresponding to at least one or more of commissure width, curvature of lower lip, incisor display dimension, philtrum length, crown height, gingiva display, lip incompetence, and facial symmetry.

In further embodiments, the aesthetic smile has a consonant smile arc, wherein the application provides weightings to one or more factors selected from a group consisting of smile index, incisor display, commissure width, philtrum length, crown height, incisor at rest characteristics, gingiva display on smile characteristics, lip incompetence and facial symmetry, to generate a composite score for the aesthetic smile.

In additional embodiments, the set of rules quantifies a smile by using macro-aesthetics rules, mini-aesthetics rules, and micro-aesthetics rules.

In yet additional embodiments, the macro-aesthetics rules relate to one or more factors selected from a group consisting of profile, lip fullness, chin projection, nasal base width, nasofrontal angle, vertical proportions, intercanthal distance, nasal projection, pupil-midfacial distance, and nasolabial angle.

In further embodiments, the mini-aesthetics rules relate to one or more factors selected from a group consisting of incisor display, crowding, smile symmetry, transverse smile, gingival display, vermilion display, smile arc, occlusal space cant, and buccal corridor.

In yet further embodiments, the micro-aesthetics rules relate to one or more factors selected from a group consisting of tooth shape, incisor angulations, tooth height and width relationship, relative proportions central incisor, lateral incisor, canine, and first premolar, tooth shade, gingival height, emergence profile, and spacing.

In additional embodiments, in order to generate an aesthetic smile, the orthodontic appliance is designed to perform changing of tooth positioning via appliance parameters to change transverse smile characteristics.

In additional embodiments, in order to generate an aesthetic smile, the orthodontic appliance is designed to perform correcting of flat smile via changing appliance parameters to at least extrude maxillary incisors.

In additional embodiments, in order to generate an aesthetic smile, the orthodontic appliance is designed to perform generation of broader smile via broader arch wires.

In additional embodiments, in order to generate an aesthetic smile, the orthodontic appliance is designed to perform correcting of dental crowding via expansion of arch.

In additional embodiments, in order to generate an aesthetic smile, the orthodontic appliance is designed to perform correcting of excessive mandibular incisor protrusion.

Provided also are a method, system, and computer program product in which a clinic site device sends dental information of a patient to a computational device maintained at a site controlled by an appliance manufacturer, wherein the clinic site device is coupled to the computational device via a network. A tentative treatment plan generated by the computational device is received. A sequence of dental information based on which the tentative treatment plan was generated by the computational device is also received, wherein the tentative treatment plan is for generating an orthodontic appliance for an aesthetic smile determined by a set of rules associated with an application maintained in the computational device.

In certain embodiments, a determination is made as to whether the tentative treatment plan is appropriate, by reviewing the tentative treatment plan and the sequence of images. In response to determining that the tentative treatment plan is appropriate, an approval notification is sent, wherein the approval notification approves the tentative treatment plan.

In further embodiments, in response to determining that the tentative treatment plan is not appropriate, the tentative treatment plan is modified to redesign the orthodontic appliance.

In yet further embodiments, a simulated three-dimensional view of a smile of the patient is displayed to the patient, wherein the three-dimensional view of the smile of the patient is received from the computational device.

In additional embodiments, the dental information comprises at least one of photographic imagery, digital video imagery, intra-oral scan imagery, cone beam computed tomography imagery, X-ray imagery, magnetic resonance imagery, ultrasound imagery, and electron beam imagery, wherein the dental information includes images of soft tissue, hard tissue, and teeth of the patient.

In further embodiments, the treatment plan is based on a computed parameter that is based at least on one measured value that is a commissure width and at least on one rule of the set of rules that relates the commissure width to a dimension of the orthodontic appliance.

In yet further embodiments, the computed parameter is configured to allow the patient employing the orthodontic appliance on the teeth to achieve a smile in conformance with a selected aesthetics rule maintained in the set of rules.

In certain embodiments, the clinic site device sends to the computational device, general case preferences from a dental practitioner during registration of the dental practitioner, wherein the general case preferences include at least one of appliance preferences, torque values, and end of treatment preferences.

BRIEF DESCRIPTION OF THE DRAWINGS

Referring now to the drawings in which like reference numbers represent corresponding parts throughout.

DETAILED DESCRIPTION

In the following description, reference is made to the accompanying drawings which form a part hereof and which illustrate several embodiments. It is understood that other embodiments may be utilized and structural and operational changes may be made.

Exemplary Embodiments

Figure 1:
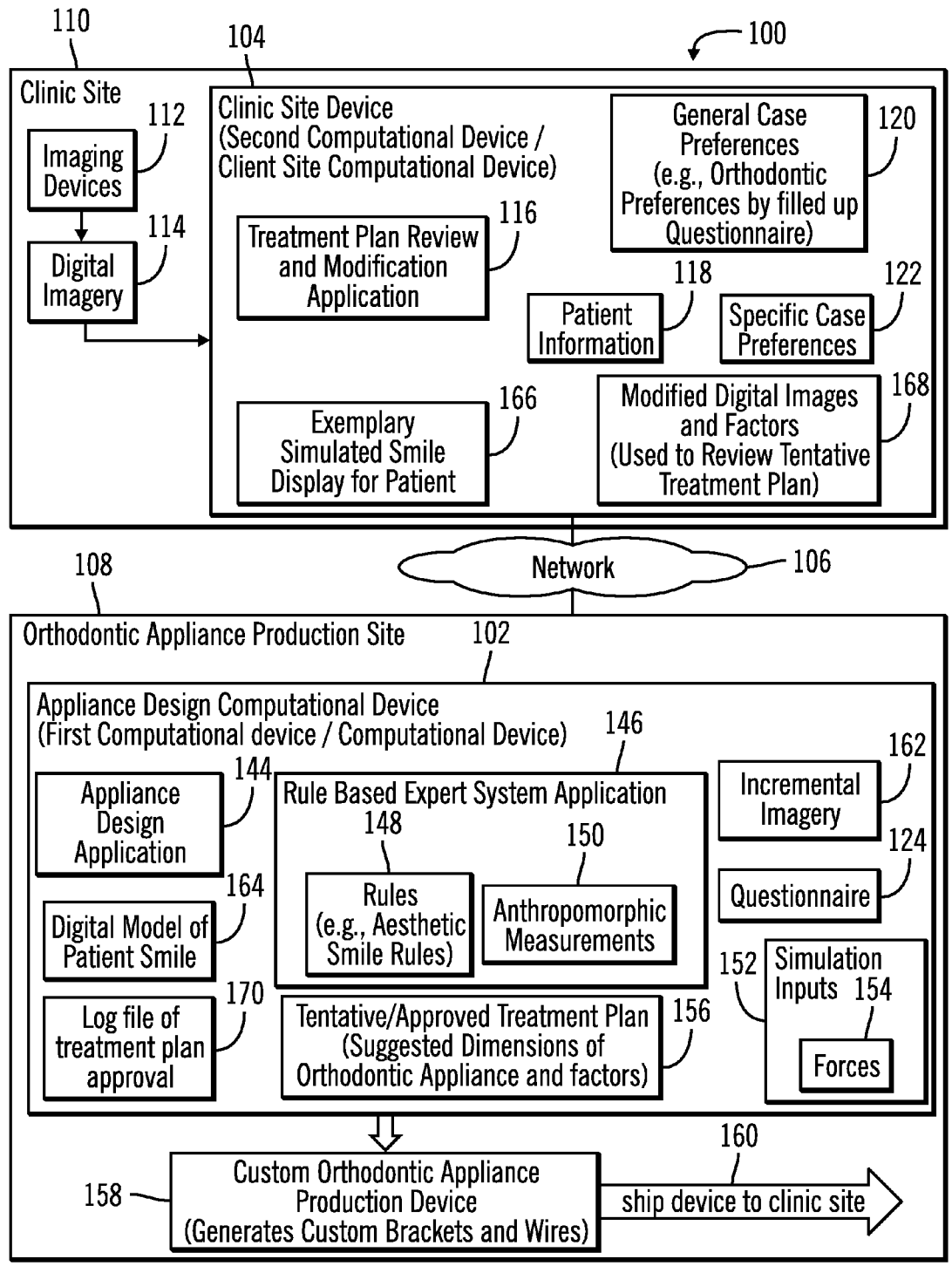
FIG. 1 illustrates a block diagram of a computing environment that at least includes an appliance design computational device coupled to a clinic site device over a network, in accordance with certain embodiments.

FIG. 1 illustrates a block diagram of a computing environment 100 that at least includes an appliance design computational device 102 coupled to a clinic site device 104 over a network 106, in accordance with certain embodiments.

The appliance design computational device 102 and the clinic site device 104 include any suitable computational device, such as, a personal computer, a workstation, a server, a mainframe, a hand held computer, a palm top computer, a telephony device, a network appliance, a blade computer, a server, or any device capable or receiving or transmitting information. The network 106 coupling the appliance design computational device 102 and the clinic site device 104 may comprise any suitable network, such as the Internet, a wide area network, a peer-to-peer network, a client-server network, etc. The client site device 104 is also referred to as a clinic site computational device 104.

In certain embodiments, the appliance design computational device 102 may be located in an orthodontic appliance production site 108 and the clinic site device 104 may be located in a clinic site 110. The orthodontic appliance production site 108 may be a facility, building, campus, plant, etc., directly or indirectly controlled by the manufacturer or designer of an orthodontic device, such as an orthodontic brace. The clinic site 110 may be a dentist's office, an orthodontist's office, a dental hospital, a clinic, an imaging center, etc. A dental practitioner, such as an orthodontist, dentist, dental assistant, or other person interested in creating an orthodontic appliance, may use the clinic site device 104 to generate a prescription for an orthodontic appliance. In certain embodiments, the orthodontic appliance production site 108 and the clinic site 110 may be separated by distances of over a kilometer and the network 106 may provide the communications infrastructure coupling the orthodontic appliance production site 108 and the clinic site 110.

The clinic site 110 may include a plurality of imaging devices 112, such as various image capturing devices, such as still cameras, video cameras, intra-oral (I/O) scanners, cone beam scanners, X-ray machines, magnetic resonance imagery (MRI) machines, ultrasound machines and other imaging devices (e.g., electron beam imaging devices). The dental practitioner may use the imaging devices 112 to generate digital imagery 114 of the patient's teeth, jaws, soft tissue, and other features.

The clinic site device 104 may include a treatment plan review and modification application 116. The treatment plan review and modification application 116 may be implemented in software, hardware, firmware or combination thereof and may be executed via one or more processors in the clinic site device 104.

In addition to the treatment plan review and modification application 116, the clinic site device 104 includes data structures that store patient information 118, general case preferences 120, and specific case preferences 122. Patient information 118 stores information related to each of a plurality of patients. The patient information 118 may include the name, date of birth, age, ethnicity, and other personal characteristics of each of the patients. The general case preferences 120 may be generated by the dental practitioner by filling up a questionnaire 124 provided by a manufacturer of orthodontic devices. The general case preferences 120 may include some parameters that are to be used in the design of orthodontic appliances for all patients of a dental practitioner. The specific case preferences 122 may include parameters that are to be used in the design of an orthodontic appliance for a particular patient.

In certain embodiments, the treatment plan review and modification application 116 receives a questionnaire 124 from the appliance design computational device 102 requesting general case preferences for the design of orthodontic appliances for all patients. The dental practitioner may complete the questionnaire 124, and the general case preferences 120 may be transmitted to the appliance design computational device 102. The dental practitioner does not have to modify the general case preferences 120 for every patient.

When a new patient arrives for orthodontic treatment, the dental practitioner may capture digital imagery 114 via the imaging devices 112 at the clinic site 110, and send the specific case preferences 122 for design of an orthodontic appliance for the new patient to the appliance design computational device 102. In certain embodiments, the completion of the questionnaire 124, the generation of the general case preferences 120, and the generation of the specific case preferences 122 may be performed by the dental practitioner by using the treatment plan review and modification application 116.

In addition to the patient information 118 and the specific case preferences 122, the clinic site device 104 also sends the digital imagery 114 to the appliance design computational device 102 located at the orthodontic appliance production site 108.

The appliance design computational device 102 receives the patient information 118, the specific case preferences 122, and the digital imagery 114 from the client site computational device 104. The appliance design computational device 102 includes an appliance design application 144 and a rule based expert system application 146. The rule based expert system application 146 has a set of rules 148 and a set of anthropomorphic measurements 150 with respect to which the set of rules 148 may be applied. Values for the anthropomorphic measurements 150 may be generated by the rule based expert system application 146 by analyzing the dental imagery 114 received form the clinic site device 104. Software components within the appliance design computational device 102 may be used to generate models of the head, teeth, soft and hard tissue, muscle, blood vessels, etc., based at least on digital imagery 114 received from the clinic site device 104.

Data structures that correspond to simulation inputs 152 such as forces 154 to be applied on elements of the orthodontic appliance are also maintained in the appliance design computational device 102. The appliance design application 144 interacts with the rule based expert system application 146 and the simulation inputs 154 to generate a tentative treatment plan 156 that is to be sent to the clinic site device 104 for review by the dental practitioner. The tentative treatment plan 156 may include suggested dimensions for the orthodontic appliance and factors used to design the orthodontic appliance at the appliance design computational device 102. After one or more interactions with the dental practitioner via the clinic site device 104, a final prescription is determined. The final prescription may be referred to as an approved treatment plan 156. The approval of the treatment plan is performed by the dental practitioner at the clinic site 110.

The approved treatment plan 156 is used by the appliance design computational device 102 to generate a design for a custom orthodontic appliance for a patient. In certain countries in which regulatory or other reasons prohibit or make it impractical for the final prescription to be determined without approval of a dental practitioner, the approval of the dental practitioner is obtained to generate the approved treatment plan 156.

The generated design for the custom orthodontic appliance is sent from the appliance design computational device 102 to a custom orthodontic appliance production device 158 that is configured to manufacture an orthodontic appliance, such as custom brackets, trays, retainers, aligners, braces, wires, etc., corresponding to the generated design. The custom orthodontic appliance production device 158 may comprise specialized equipment including a computer numerically controlled machine tool for manufacturing orthodontic appliances. In certain embodiments, the custom orthodontic appliance production device 158 is located in the orthodontic appliance production site 108 and is coupled to the appliance design computational device 102 via a network such as the Internet, an intranet, a local area network, etc.

Therefore, FIG. 1 illustrates certain embodiments that show information exchanged between the clinic site device 104 and the appliance design computational device 102 to generate potential improvements to a tentative treatment plan 156 and to design a custom orthodontic appliance. Once the custom orthodontic appliance is manufactured by the custom orthodontic appliance production device 158, the custom orthodontic appliance is shipped 160 to the clinic site 110.

In certain embodiments, when the appliance design computational device 102 sends a tentative treatment plan 156 to the clinic site 118 for approval by a dental practitioner, the appliance design computational device 102 may also send incremental imagery 162 and a digital model of potential patient smile 164 to the clinic site device 104. The incremental imagery 162 may includes digital imagery that include only differences from imagery already found in the clinic site 110, in order to reduce the total volume of data transmission and to increase the speed for the exchange of date. The digital model of patient smile 164 may be generated by the appliance design application 144 based on the rule based expert system application 146 and the generated treatment plan 156.

The incremental imagery 162 and the treatment plan 156 together may be used by the treatment plan review and modification application 116 to generate a data structure referred to as modified digital images and factors 168, where the factors are the basis on which the treatment plan has been generated by the appliance design application 144. The factors are provided by the appliance design computational device 102 to the clinic site device 104. The dental practitioner may use the modified digital images and factors 168 and may modify or approve the treatment plan 156, and send the modification or approval to the appliance design computational device 102. The appliance design computational device may maintain a log file of treatment plan approvals 170 for regulatory purposes or for recordkeeping.

In certain embodiments, the clinic site device 104 may receive the treatment plan 156 and the digital model of patient smile 164, and may store the digital model of patient smile 164 in a data structure referred to as exemplary simulated smile display for patient 166. Should the processing at the orthodontic application production site 108 be fast enough, the orthodontic practitioner may be able to display the exemplary simulated smile display for the patient 166 to the patient who may not have left the clinic site.

Various alternative embodiments may be employed in addition to the embodiments shown in FIG. 1. For example, in certain embodiments the computing environment 100 shown in FIG. 1 may comprise a cloud computing environment in which usage of computation, software, data access, and storage services do not require end-users to be aware of the physical location and configuration of the system that delivers the services. Cloud computing providers may deliver applications via the Internet, wherein the applications are accessed via a Web browser, while the software and data may be stored on servers at one or more remote locations. Cloud computing may encompass any subscription-based or pay per use service for accessing computation, software, data access, storage services, etc. For example, computing and storage systems located at the orthodontic appliance production site 108 may provide computation, software, data access, and storage services to users located at the clinic site 100 in a cloud computing environment. Similarly, computing and storage systems located at the clinic site 110 may provide computation, software, data access, and storage services to users at the orthodontic appliance production site 108 in a cloud computing environment.

In certain embodiments, the orthodontic application production site 108 may receive requests and orders from a plurality of clinic sites. Operators or controlling entities of the orthodontic application production site 108 may distribute the treatment plan review and modification application 116 and any other required software free of charge or for a fee to the clinic site 110 to use in generating the general case preferences 120, the specific case preferences 122, and the sending of the digital imagery 114 to the appliance design computational device 102. In other embodiments, operators or controlling entities of the orthodontic application production site 108 may provide authorization for execution of the treatment plan review and modification application 116 and any other required software over a cloud computing environment to users at the clinic site 110. Additionally, operators or controlling entities of the orthodontic appliance production site 108 may provide the equipment needed to produce the approval or modifications of the treatment plans, and dental imagery equipment, such as cameras and scanners, for free or at a reduced price. For example, operators or controlling entities of the orthodontic application production site 108 may provide monthly or yearly subscription-based services, payment per use services, prepaid, or invoicing based services, etc., over a cloud computing environment to users at the clinic site 110. It is envisaged that many different types of business or commercial relationships may be established between operators or controlling entities of the orthodontic appliance production site 108 and dental practitioners at the clinic site 110 for providing cloud computing or network based computing services.

Figure 2:
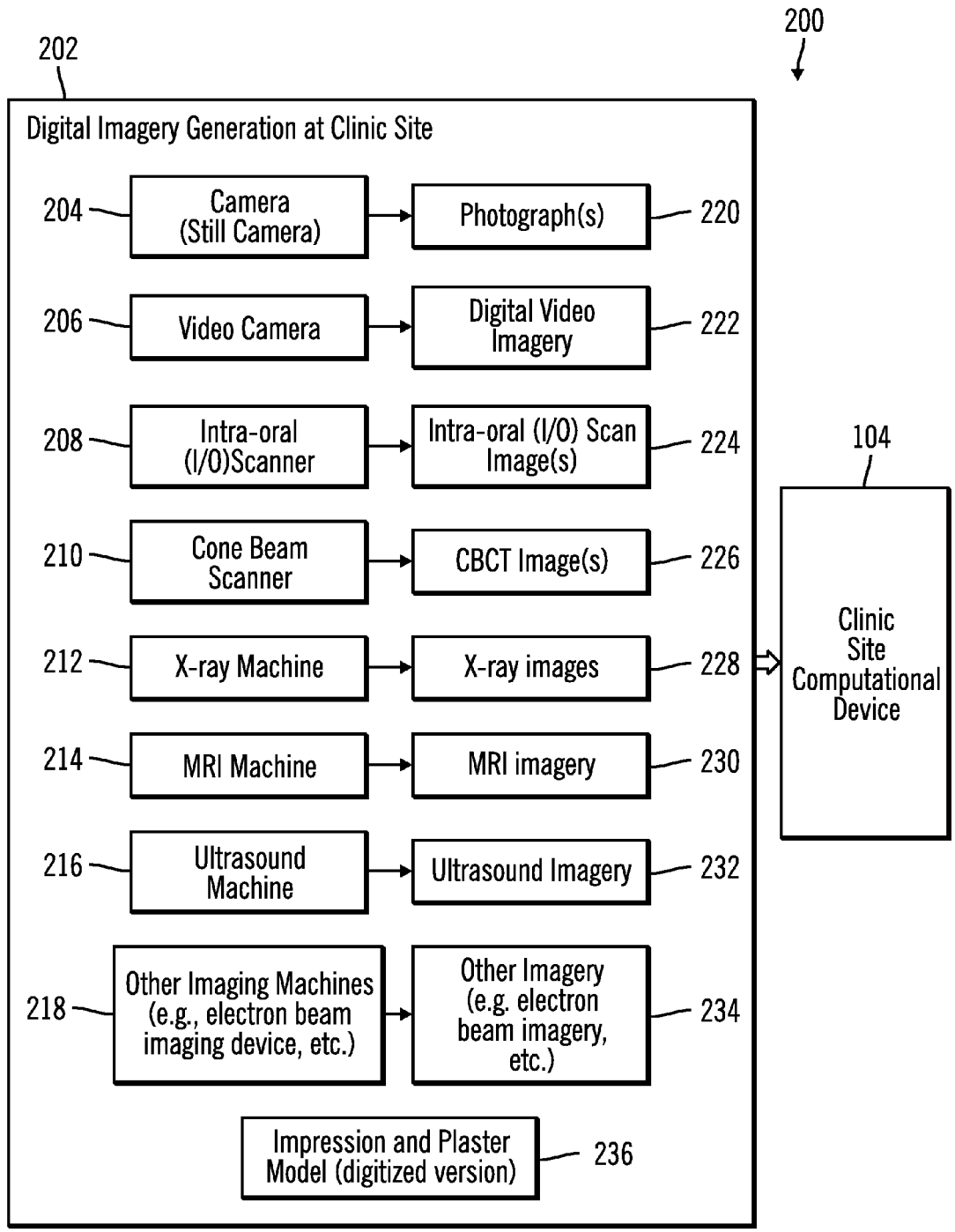
FIG. 2 illustrates a block diagram that shows a plurality of mechanisms for generating digital imagery at the clinic site, in accordance with certain embodiments.

FIG. 2 illustrates a block diagram 200 that shows a plurality of mechanisms 202 for generating digital imagery 114 at the clinic site 110, in accordance with certain embodiments.

The clinic site 110 may include a plurality of imaging devices, such as various image capturing devices, such as still cameras 204, video cameras 206, intra-oral (I/O) scanners 208, cone beam scanners 210, X-ray machines 212, magnetic resonance imagery (MRI) machines 214, ultrasound machines 216 and other imaging devices 218, such as electron beam imaging devices.

The dental practitioner may use the still camera 204 and or the video camera 206 to take a plurality of photographs 220 and digital video imagery 222 of the patient to show the patients head, face, teeth, etc. The photographs 220 and video imagery 222 may also capture the smile or laughter of the patient, and the orientation of the patient's teeth in different facial expressions of the patient. The dental practitioner may use the intra-oral scanner 208 to take intra-oral scan images 224 of the teeth and surrounding structures of the patient.

In certain embodiments, the dental practitioner uses the cone beam scanner 210 to acquire a plurality of cone beam computed tomography images 226 at a plurality of positions and orientations of the patient's teeth and head, The cone beam computed tomography images 226 may include the bone structure, soft tissue, muscle, blood vessels, etc., that are proximate to the teeth. For example, cone beam computed tomography images 226 may show cross-sections of the teeth, lips, upper jaw, lower jaw, the cranium, the tongue, etc.

In certain embodiments the X-ray machine 212 may be used to generate X-ray images 228 of the patient's teeth, bones, and other structures. The Magnetic Resonance Imaging (MRI) machine may be used to generate MRI imagery 230, and the ultrasound machine 216 may be used to generate ultrasound imagery 232 of the teeth, bones, and other structures of the patient.

Other imaging devices 218 may also be employed by the dental practitioner to capture other imagery 234 of the teeth and surrounding features. The images of the teeth and surrounding features may be taken in various positions of the teeth of the patient. For example, the images may be taken both when the patient has a neutral expression on the face and when the patient has a smiling expression on the face.

Additionally, in certain embodiments the dental practitioner may create an impression and plaster model of the teeth and store a digitized version of the impression and plaster model 236.

In certain embodiments, the photographs 229, the digital video imagery 222, the intra-oral scan images 224, the CBCT images 226, the X-ray images 228, the MRI imagery 230, the ultrasound imagery 232, the other imagery 234, and the digitized version of the impression and plaster model 236 may be transmitted to the clinic site device 104 for storage, transmission and analysis.

Figure 3:
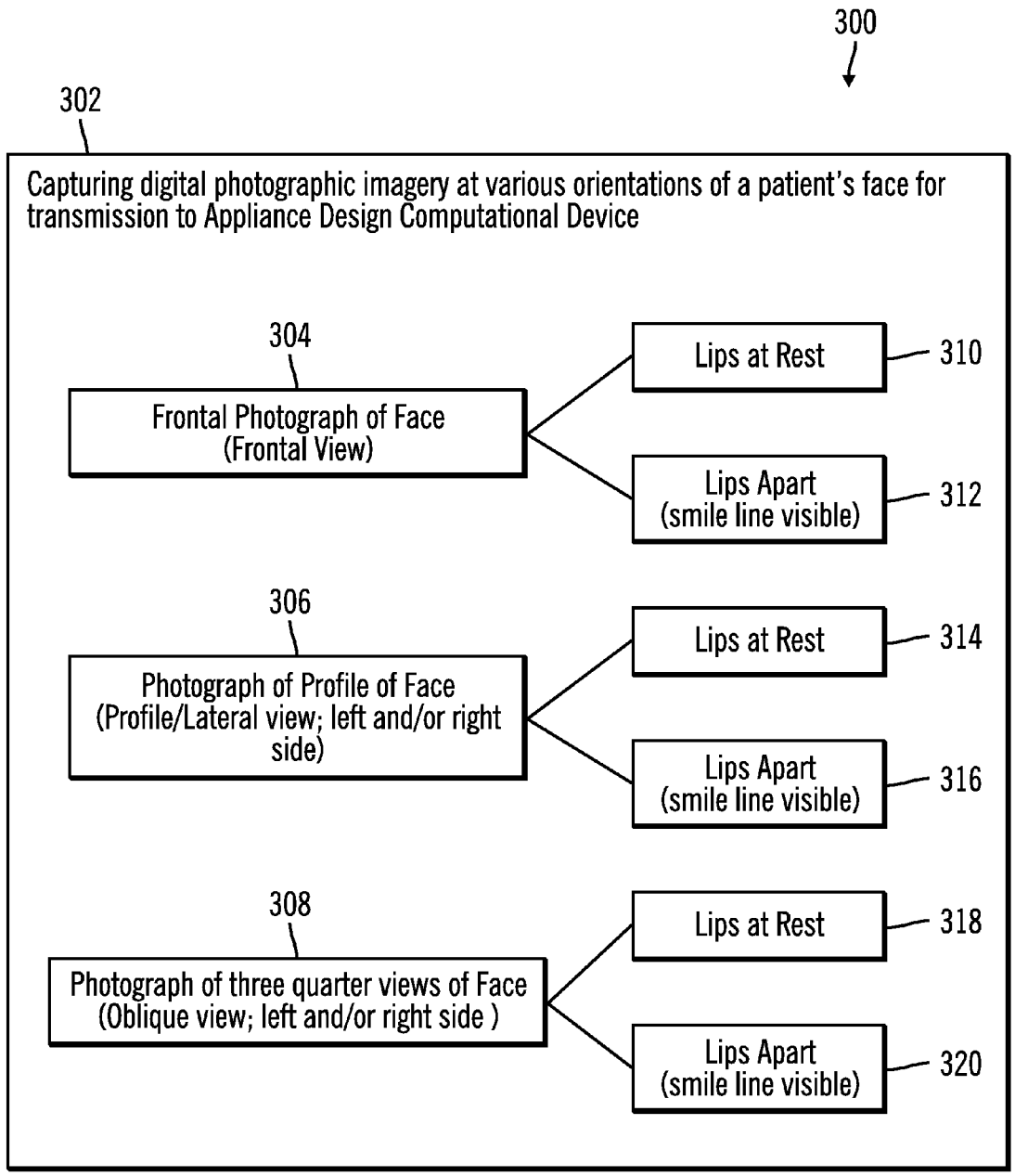
FIG. 3 illustrates a block diagram that shows how digital photographic imagery at various orientations of a patient's face is captured at the clinic site for transmission to the appliance design computational device, in accordance with certain embodiments.

FIG. 3 illustrates a block diagram 300 that shows how digital photographic imagery at various orientations of a patient's face is captured at the clinic site 110 for transmission to the appliance design computational device 102, in accordance with certain embodiments 302.

The dental practitioner may take frontal photographs of a patient's face (reference numeral 304), photographs of the profile of a patient's face (reference numeral 306), and photographs of three quarter views of a patient's face (reference numeral 308). In each case the photographs may be captured when the patient's lips are at rest and when the lips are apart (reference numerals 310, 312, 314, 316, 318, 320). When the lips are apart the smile line of the patient may be visible. It may be noted that that the photographs of the profile of the face may be captured from both the left and/or the right side of the patient, and the photographs of the three quarter views of the face may also be captures from the left and/or right side of the patient.

Figure 4:
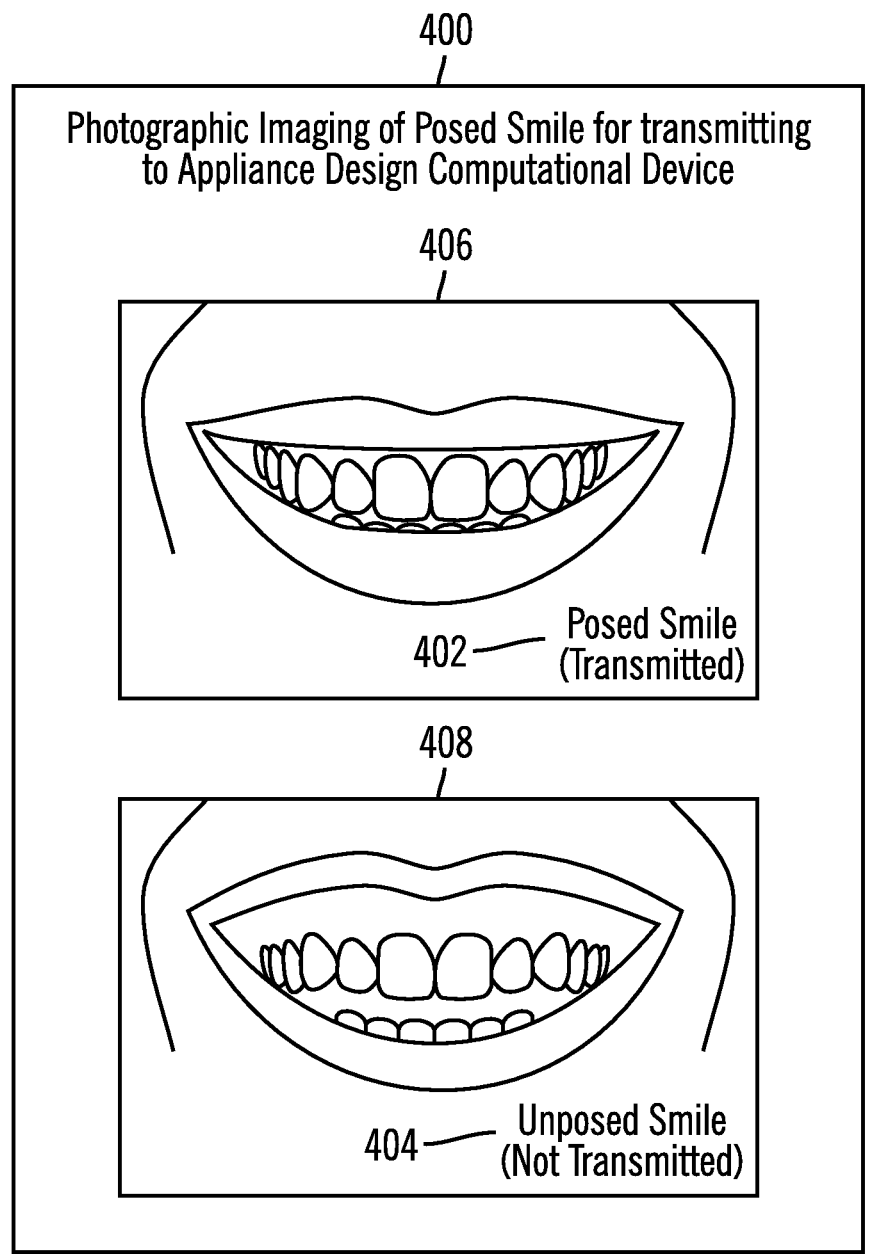
FIG. 4 illustrates a block diagram that shows transmission of digital photographic imagery of a posed smile captured at the clinic site for transmission to the appliance design computational device, in accordance with certain embodiments.

FIG. 4 illustrates a block diagram 400 that shows transmission of digital photographic imagery of a posed smile captured at the clinic site 110 for transmission to the appliance design computational device 102, in accordance with certain embodiments.

The posed smile 402 of an exemplary patient is shown in diagram 406, whereas an unposed smile 404 is shown in diagram 408. The posed smile 402 of a patient is the one that is suitable for use in manufacturing orthodontic appliance, and digital photographs and digital video imagery corresponding to posed smiles of patients are transmitted from the clinic site device 104 to the appliance design computational device 102. Photographs that show unposed smiles of the patient may be discarded by the dental practitioner.

Figure 5:
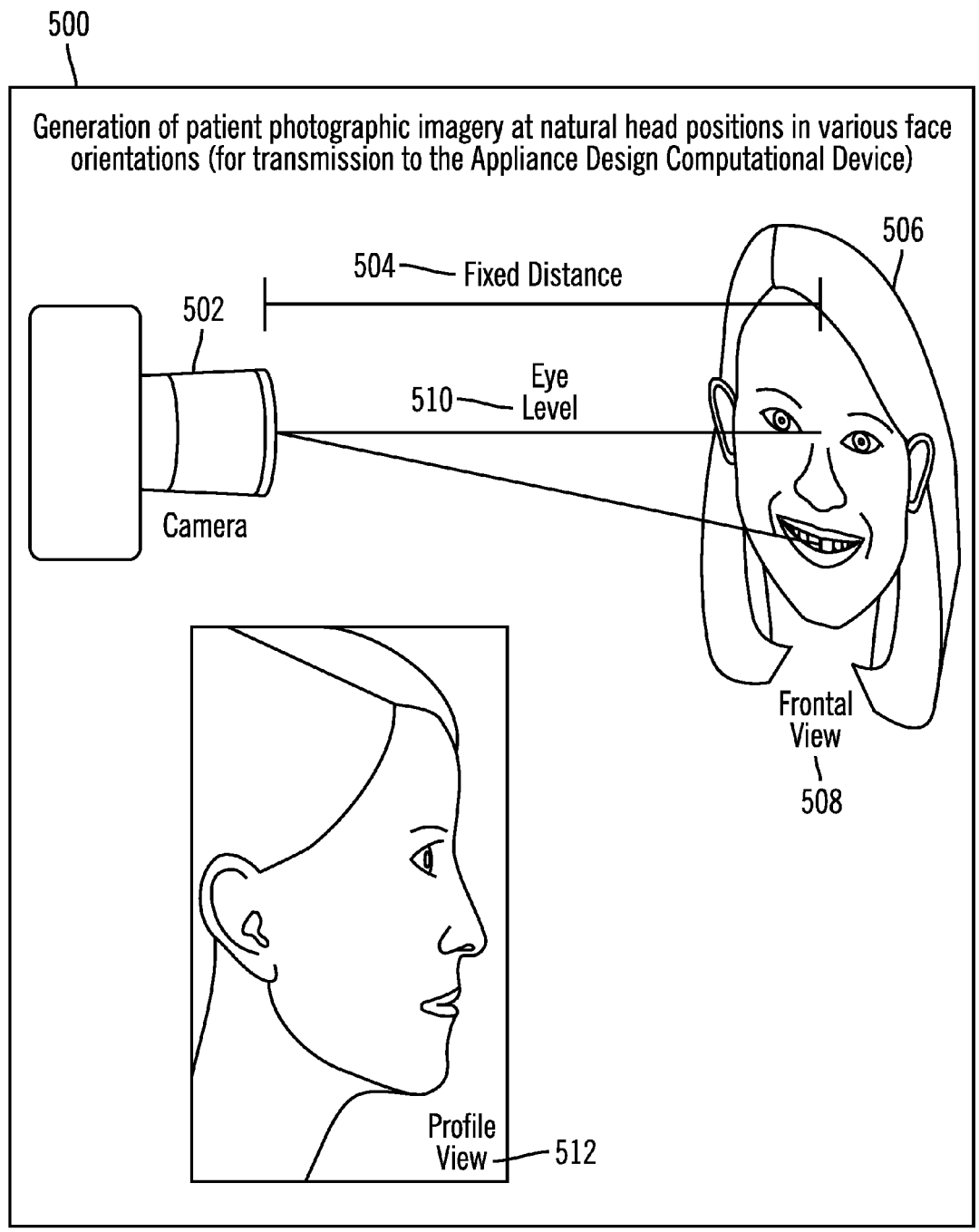
FIG. 5 illustrates a block diagram that shows generation of patient photographic imagery at natural head positions in various face orientations for transmission to the appliance design computational device, in accordance with certain embodiments.

FIG. 5 illustrates a block diagram 500 that shows generation of patient photographic imagery at natural head positions in various face orientations for transmission to the appliance design computational device 102, in accordance with certain embodiments.

A camera 502 may be placed at a fixed distance 504 from a patient 506 who is placed in a frontal view 508 to the camera. The camera may be placed at the eye level of the patient. The camera 502 may also be used to take profile views 512 of the patient. The placement of the camera 502 at a fixed distance 504 in a particular orientation to the patient allows the appliance design application 144 to determine dimensions of the various features of the patient's face via an analysis of the photographs.

Figure 6:
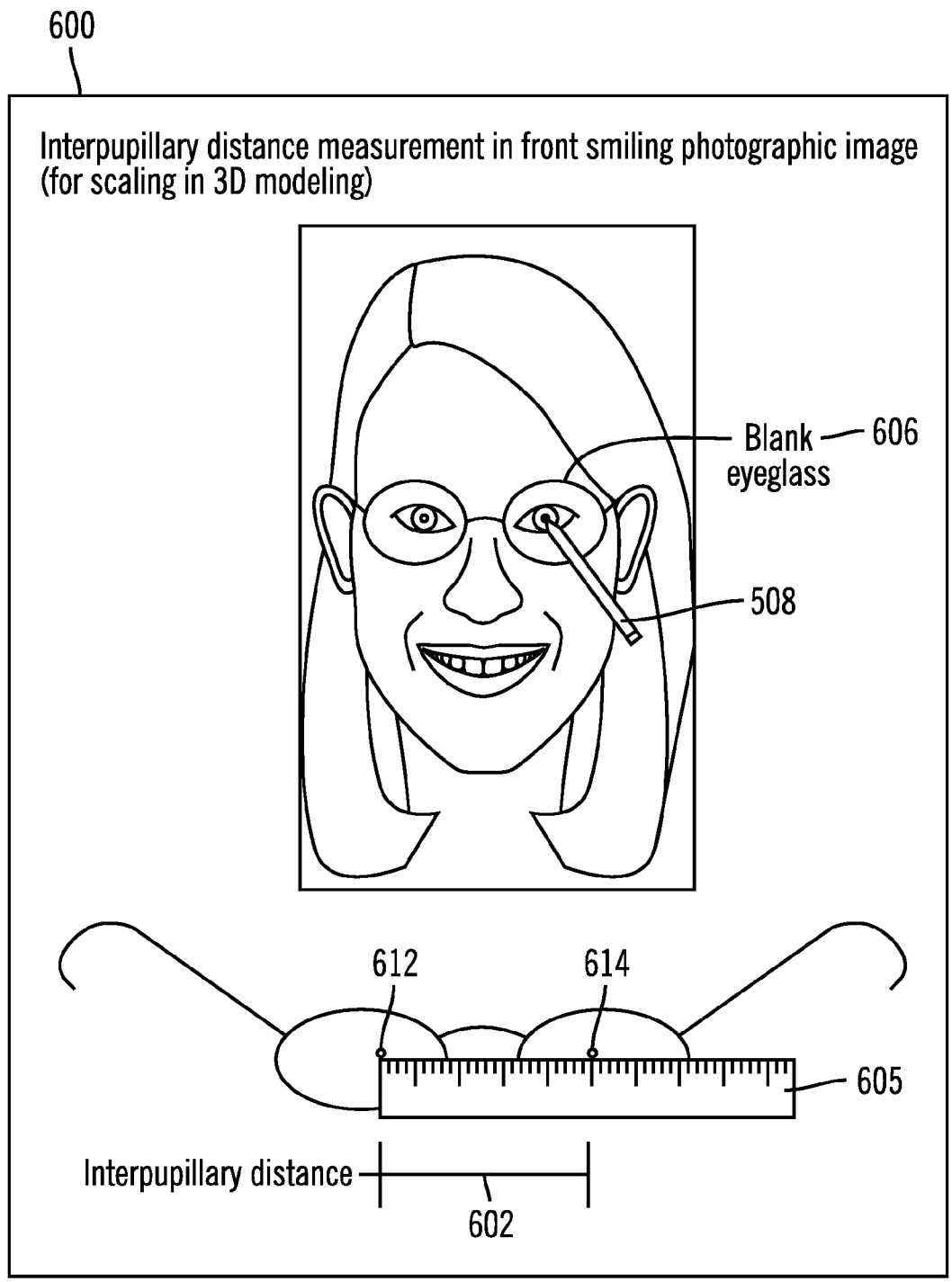
FIG. 6 illustrates a block diagram that shows certain embodiments for the measurement of interpupillary distance at the time of taking a front smiling digital photographic image at the clinic site for transmission to the appliance design computational device, in accordance with certain embodiments.

FIG. 6 illustrates a block diagram 600 that shows certain embodiments for the measurement of interpupillary distance 602 at the time of taking a front smiling digital photographic image at the clinic site 110 for transmission to the appliance design computational device 102, in accordance with certain embodiments. The interpupillary distance 602 is the distance between the pupil of the left eye and the right eye of the patient. A blank eyeglass 606 may be put on a patient and a pencil 608 may be used to mark dots (referred to as pupil markings 612, 614) on the lenses of the eyeglass corresponding to the locations of the pupils of the patient. The interpupillary distance 602 may be measured via a ruler 504 and is the distance between the two pupil markings 612, 514. The interpupillary distance 602, the fixed distance 504 of the camera 502 from the patient, the orientation of the camera, and internal camera calibration parameters allow the appliance design application 144 to determine the dimensions of various features of a patient, including dimensions of lips, size of each tooth, etc.

Figure 7:
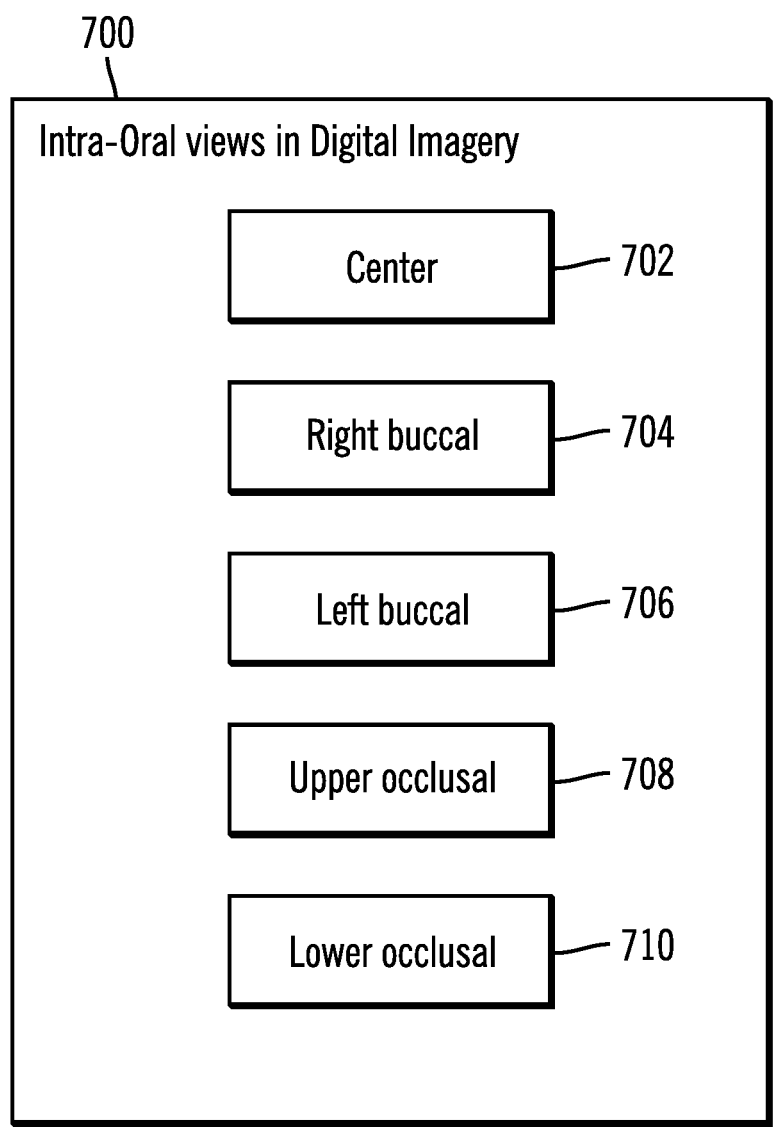
FIG. 7 illustrates a block diagram that shows certain intra-oral views in digital imagery, in accordance with certain embodiments.

FIG. 7 illustrates a block diagram 700 that shows certain exemplary intra-oral views in digital imagery 114, in accordance with certain embodiments. In certain embodiments a dental practitioner may use the intra-oral scanner to capture intra-oral images that include the center view 702, the right buccal view 704, the left buccal view 706, the upper occlusal view 710, and the lower occlusal view 710 of the oral cavity of the patient. The intra-oral images may be transmitted by the clinic side computational device 104 to the appliance design computational device 102.

Figure 8:
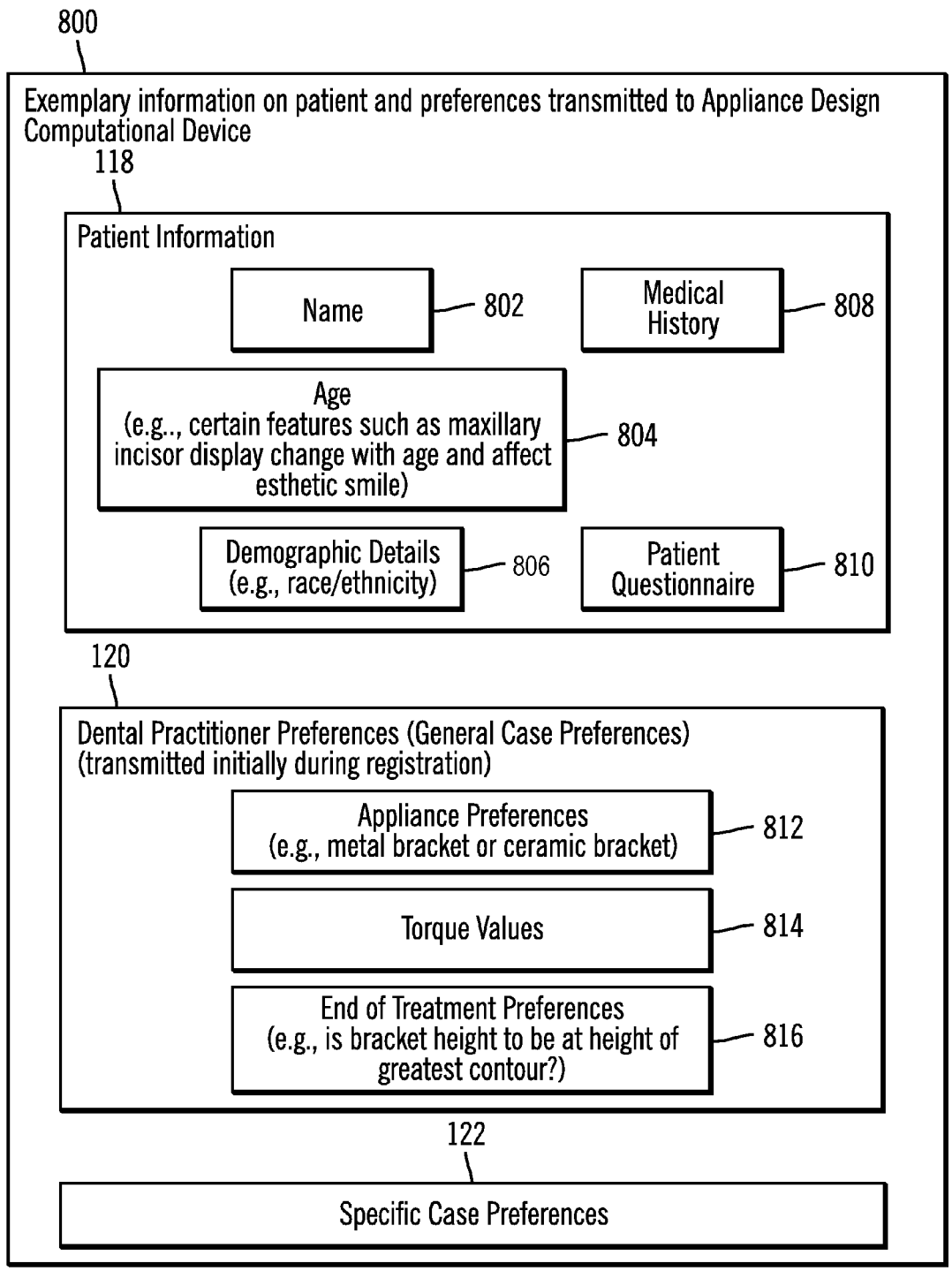
FIG. 8 illustrates a block diagram that shows certain exemplary information on a patient, and preferences transmitted to the appliance design computational device, in accordance with certain embodiments.

FIG. 8 illustrates a block diagram 800 that shows certain exemplary patient information 118 and case preferences 120, 122 transmitted to the appliance design computational device 102, in accordance with certain embodiments.

The patient information 118 may include the name 802, age 804, and demographic details 806 of the patient. The age of the patient may be important as certain features such as maxillary incisor display may change with age and may affect the aesthetics of smile. For certain patients, the maxillary incisor display which is important for attaining desired smile decreases with age, as lips move downwards and more of the mandibular incisor is shown.

The demographic details 806 may include the ethnicity of the patient, as parameters for designing appliances for an aesthetic smile may vary from one ethnic group to another.

Additionally, in certain embodiments the medical history 808 of the patient may also be transmitted to the appliance design computational device 102. Furthermore, the patient may be requested to fill up a patient questionnaire 810 that may also be transmitted as part of the patient information 118 to the appliance design computational device 102.

The preferences 120, 122 that are sent to the appliance design computation device 102 may include dental practitioner preferences 120 that are general case preferences transmitted initially during registration of a dental practitioner. Foe example, a dental practitioner may indicate appliance preferences 812, torque values 814, and end of treatment preferences 816. Exemplary appliance preferences 812 may indicate whether the dental practitioner prefers metal brackets or ceramic brackets. An exemplary end of treatment preference 816 may indicate whether the bracket height is to be at the height of the greatest contour. The specific case preferences 122 include preferences for a particular patient as determined by the dental practitioner. In certain embodiments, the specific case preferences 122 may override the general case preferences 122.

Figure 9:
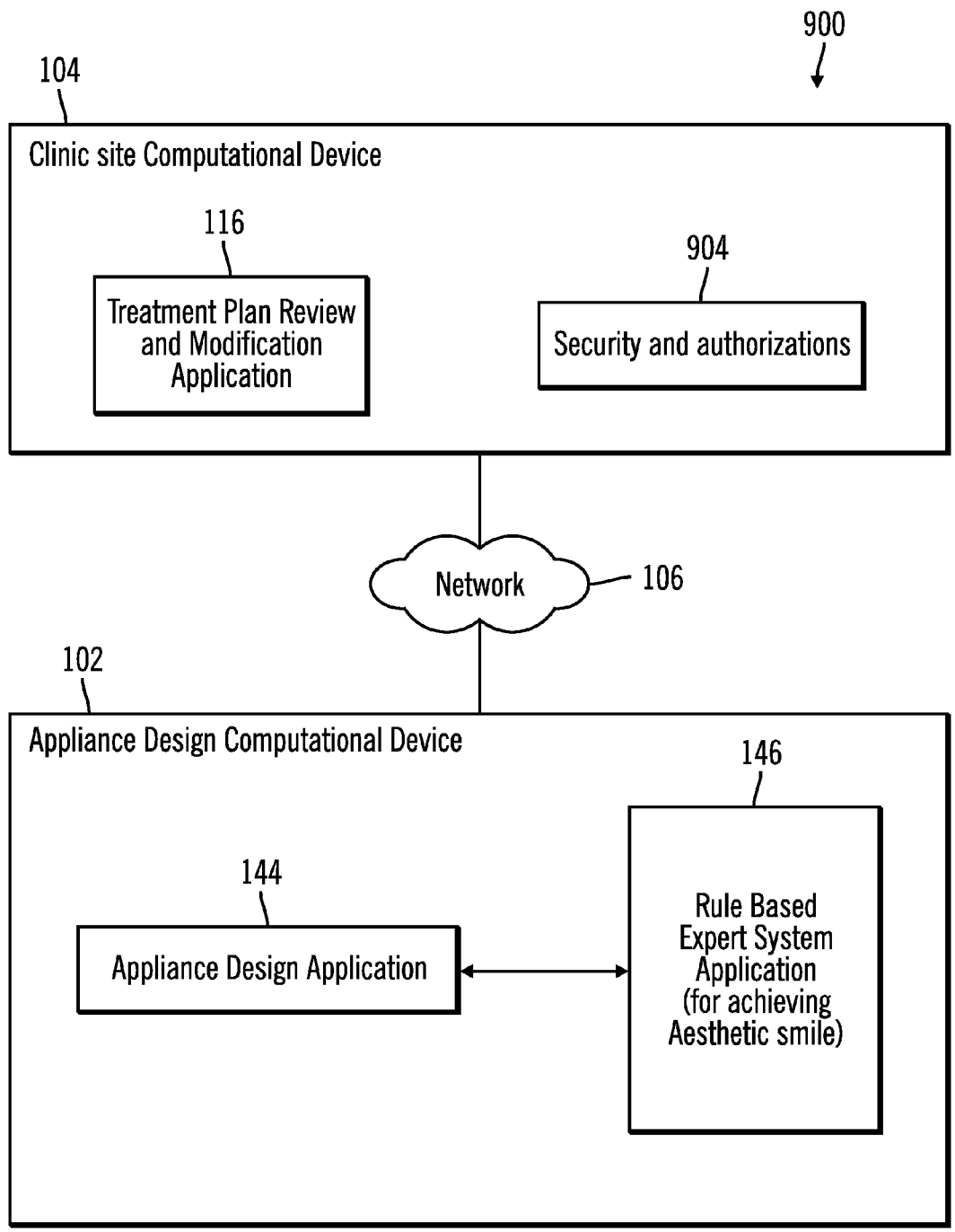
FIG. 9 illustrates a block diagram that shows interactions over a network between a client site computational device, an appliance design application and a rule based expert system application, in accordance with certain embodiments.

FIG. 9 illustrates a block diagram 900 that shows interactions over the network 106 between the clinic site device 104, an appliance design application 144 and a rule based expert system application 146, in accordance with certain embodiments;

A dental practitioner may use a treatment plan review and modification application 116 executing in the client site computational device 104 to initiate interaction and exchange of information with the appliance design application 144 that executes in the appliance design computational device 102. In certain embodiments, appropriate security and authorizations 904 criteria may be enforced for access by the treatment plan review and modification application 116. The appliance design application 144 may download authorized data from the clinic site device 104, in response to the security and authorizations 904 criteria being satisfied.

Therefore, in certain embodiments the design of an orthodontic appliance by an appliance design computational device 102 is based on analysis performed via a rule based expert system application 146 and information exchange initiated via a treatment plan review and modification application 116 with the appliance design application 144.

Figure 10:
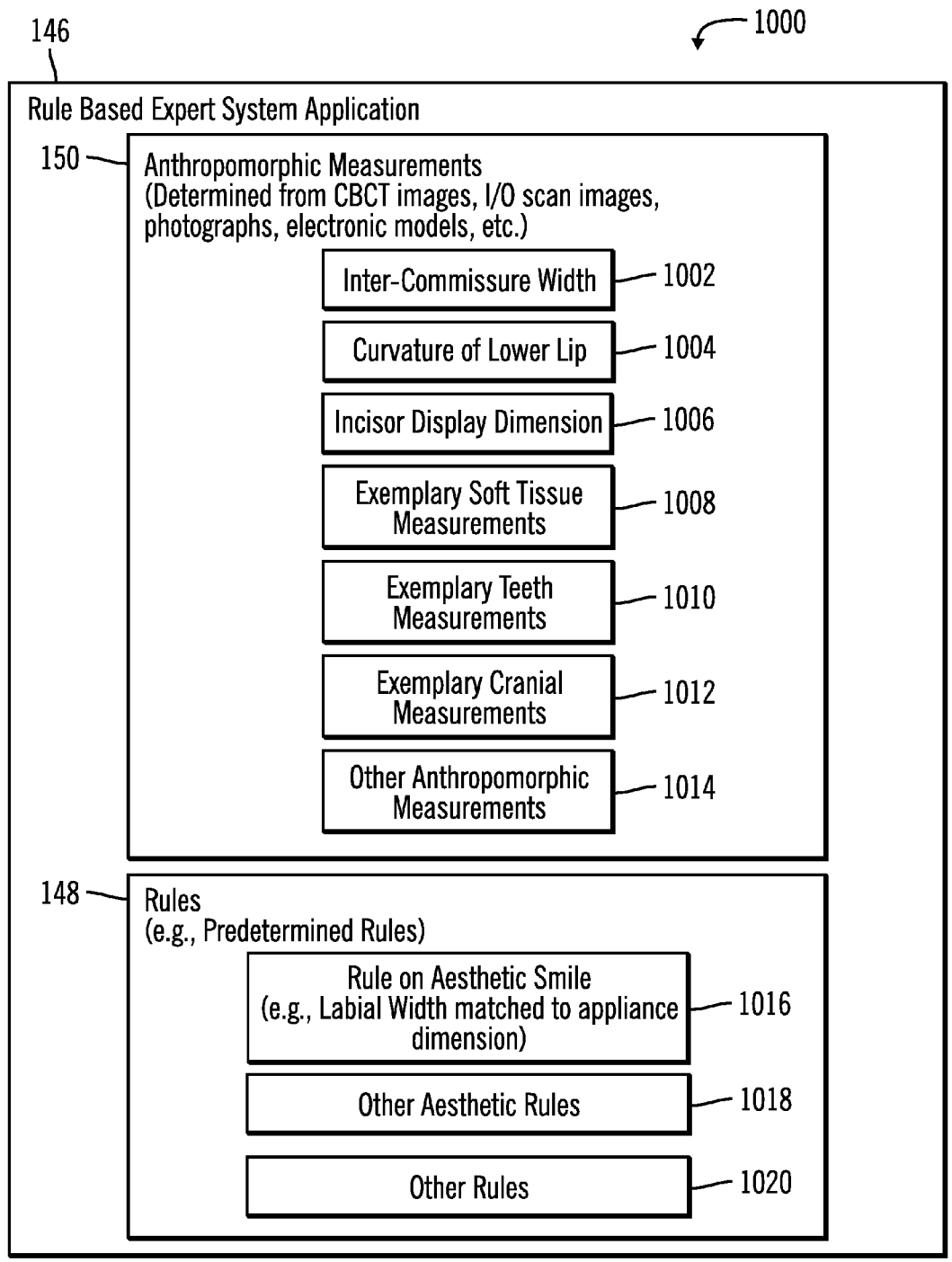
FIG. 10 illustrates a block diagram that shows a rule based expert system application, in accordance with certain embodiments.

FIG. 10 illustrates a block diagram 1000 that shows 1 elements of the rule based expert system application 146, in accordance with certain embodiments.

The anthropomorphic measurements 150 maintained by the rule based expert system application 146 include data structures that correspond to identifiers representing inter-commissure width 1002 (also referred to as commissure width), curvature of lower lip 1004, incisor display dimension 1006, exemplary soft tissue measurements 1008, exemplary teeth measurements 1010, exemplary cranial measurements 1012, and other anthropomorphic measurements 1014.

The commissure is the corner of the mouth, where the vermillion border of the superior labium (i.e., the upper lip) meets the vermillion border of the inferior labium (i.e., the lower lip). The commissure is important in facial appearance, particularly during smiling. In FIG. 10, the inter-commissure width 1002 is the distance between the two commissures of the mouth. In certain embodiments, to provide a quantitative representation to a smile, an index called the smile index may be determined. The smile index may calculated by dividing the inter-commissure width with the interlabial gap during smile, where the interlabial gap is the distance between the upper and lower lips. The smile index may be used to compare smiles.

The curvature of lower lip 1004 represents a measurement that indicates how much curved the lower lip is for a patient. The smile arc may be defined as the relationship of the curvature of the incisal edges of the maxillary (i.e., upper jaw) incisors and canines to the curvature of the lip in a posed smile. In a smile that may be desired the smile arc may be such that that the maxillary incisal edge curvature is parallel to the curvature of the lower lip 1004 upon smile, and the term consonant (i.e., ideal) may be used to describe this smile arc. A nonconsonant smile arc is one in which the maxillary incisal curvature is more than the curvature of the lower lip on smile. In certain embodiments, the goal is to achieve a consonant smile arc, and for achieving this goal the curvature of the lower lip 1004 is recorded. It is important to create or retain a consonant smile arc in a patient at the end of an orthodontic treatment procedure.

The incisor display dimension 1006 provides a measurement corresponding to displays of the incisors of the teeth. When a patient smiles, the patients may show either the entire upper incisor, or a certain percentage of the incisor. Measurement of the percentage of incisor display when combined or compared with other measurements allows certain embodiments to determine how much movement is needed for a desired smile for a patient.

The exemplary soft tissue measurements 1008 may include dimensions of muscles, etc. The exemplary teeth measurements 1010 may include the width and height of each tooth. The exemplary cranial measurements 1012 may include the length and width of the skull and orientation of the skull with respect to the teeth. The values of the various anthropomorphic measurements 150 may be populated by the rule based expert system application 146 by analyzing the digital imagery 114 sent by the clinic site device 104 to the appliance design computational device 102.

The rules 148 maintained by the rule based expert system application 146 may be provided prior to initializing the rule based expert system application 146. In certain embodiments the rules 148 may be modified after initialization of the rule based expert system application. Exemplary rules may include rules to produce an aesthetic smile 1016, other aesthetic rules 1018, and other rules 1020 that capture other aspects of orthodontics design. For example, the rule on aesthetic smile 1016 may indicate that the inter-commissure width of the patient is to be matched to the orthodontic appliance dimension. The rule based expert system application 146 analyzes the rule on aesthetic smile, and based on the already populated value in the inter-commissure width indicator 1002 provides a proper dimension for the custom orthodontic appliance that is being designed by the appliance design application 144.

Therefore, FIG. 10 illustrates an embodiment in which a rule based expert system application 146 analyzes information sent by the clinic site device 104, populates values for anthropomorphic measurements 150, and then applies the rules 148 for designing optimal orthodontic appliances.

Figure 11:
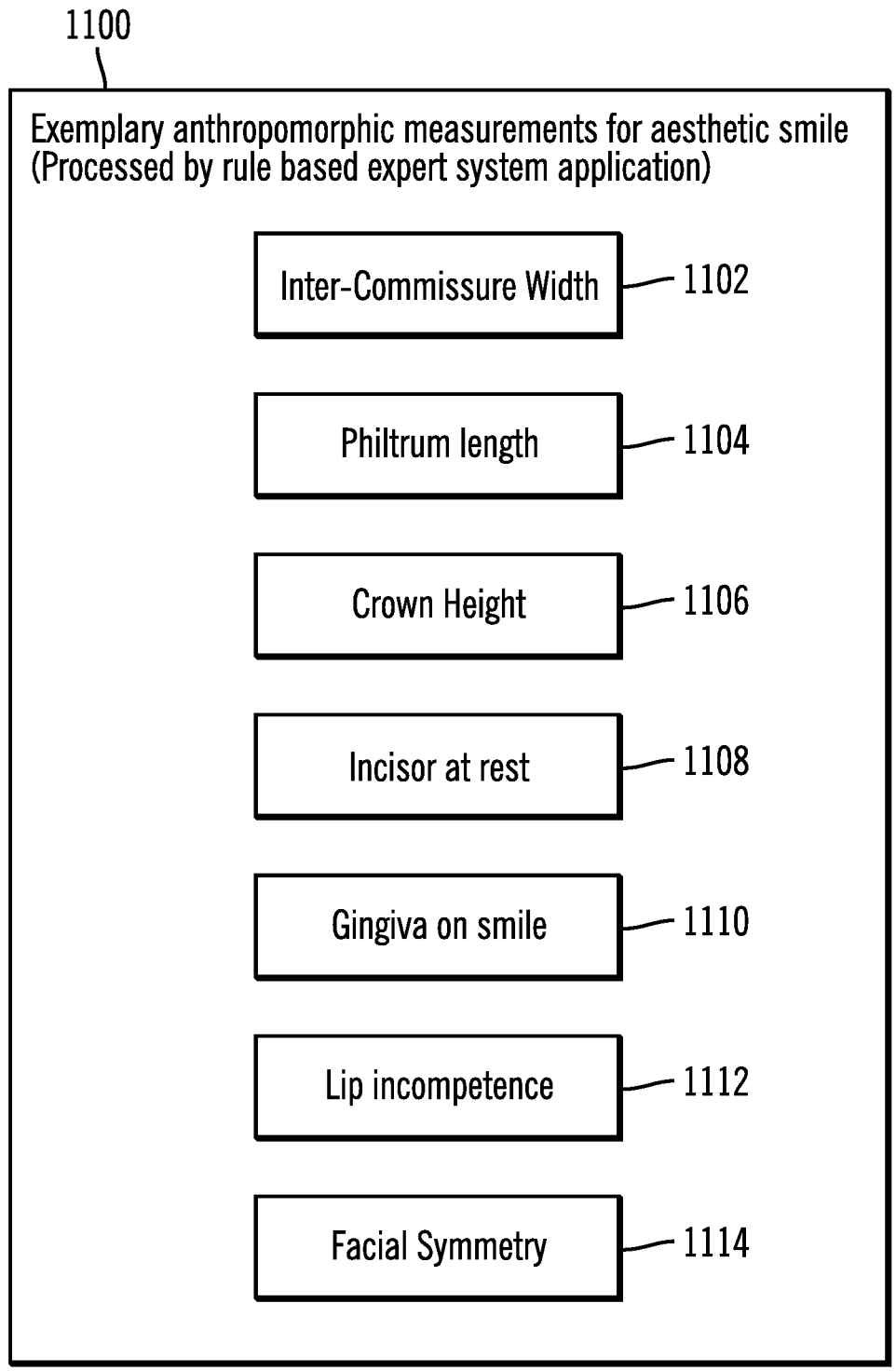
FIG. 11 illustrates a block diagram that shows exemplary anthropomorphic measurements for aesthetic smile, in accordance with certain embodiments.

FIG. 11 illustrates a block diagram 1100 that shows additional exemplary anthropomorphic measurements for aesthetic smile, in accordance with certain embodiments. The exemplary anthropomorphic measurements for aesthetic smile that are processed by the rule based expert system application 146 may include measurements on inter-commissure width 1102, philtrum length 1104, crown height 1106, incisors at rest 1108, gingiva display on smile 1110, lip incompetence 1112, facial symmetry 1114, etc. It should be noted that measurements of other attributes for generating an aesthetic smile may also be computed by analyzing the digital imagery 114 received by the appliance design computational device 102 from the clinic site device 104.

Figure 12:
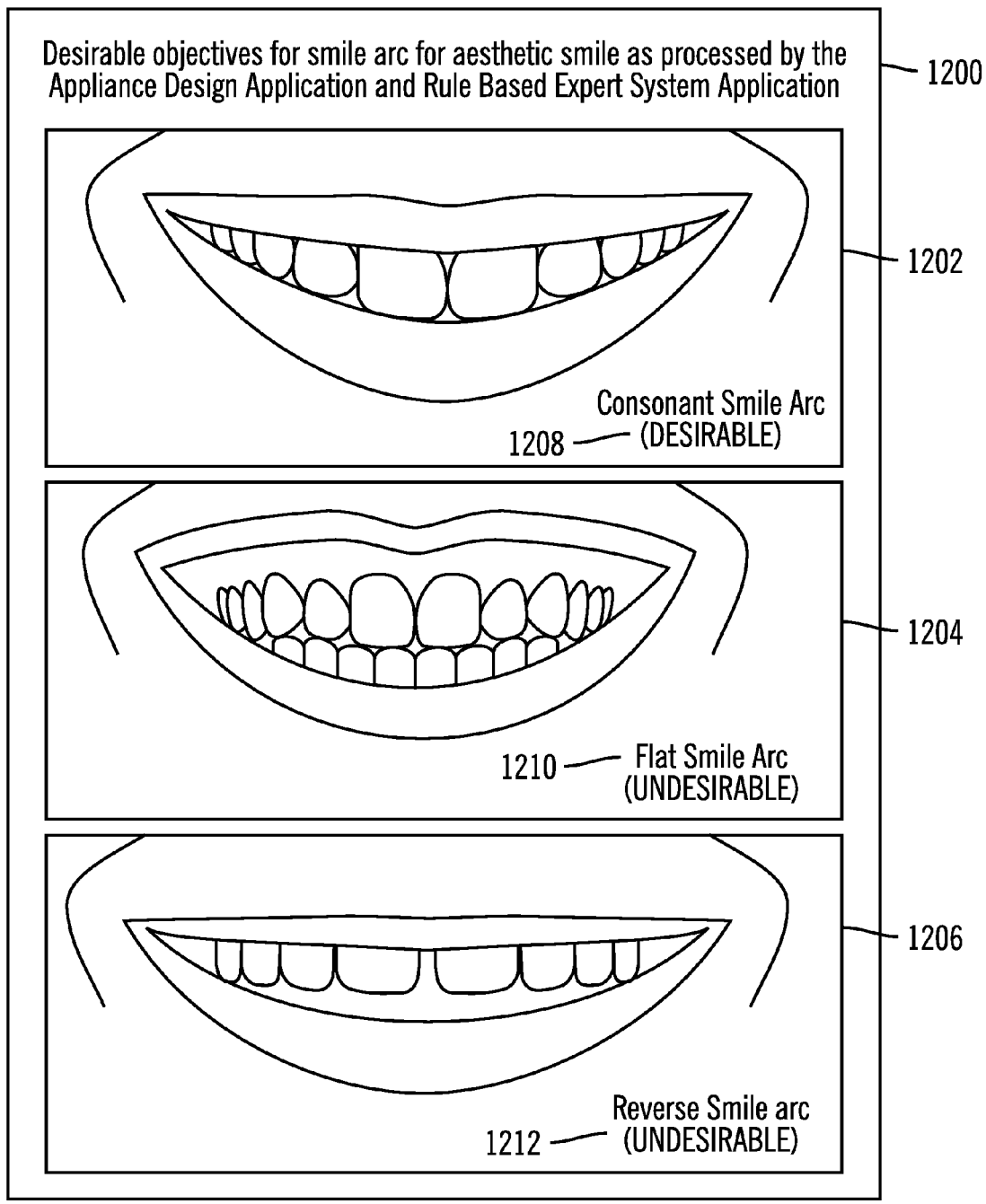
FIG. 12 illustrates a block diagram that shows desirable objectives for smile arc for aesthetic smile as processed by the appliance design application and the rule based expert system application, in accordance with certain embodiments.

FIG. 12 illustrates a block diagram 1200 that shows desirable objectives for smile arc for an aesthetic smile as processed by the appliance design application 144 and the ruled based expert system application 146, in accordance with certain embodiments.

Diagram 1202 shown in FIG. 12 displays a consonant smile arc 1208 that is desirable for an aesthetic smile. The rule based expert system application 146 has rules 148 that attempt to generate appliances that would result in a consonant smile arc 1208 for a patient. The flat smile arc 1210 shown in diagram 1204 and the reverse smile arc shown in diagram 1206 are undesirable and the rules 148 of the rule based expert system application 146 are designed to avoid such undesirable smiles in a patient after orthodontic treatment.

Figure 13:
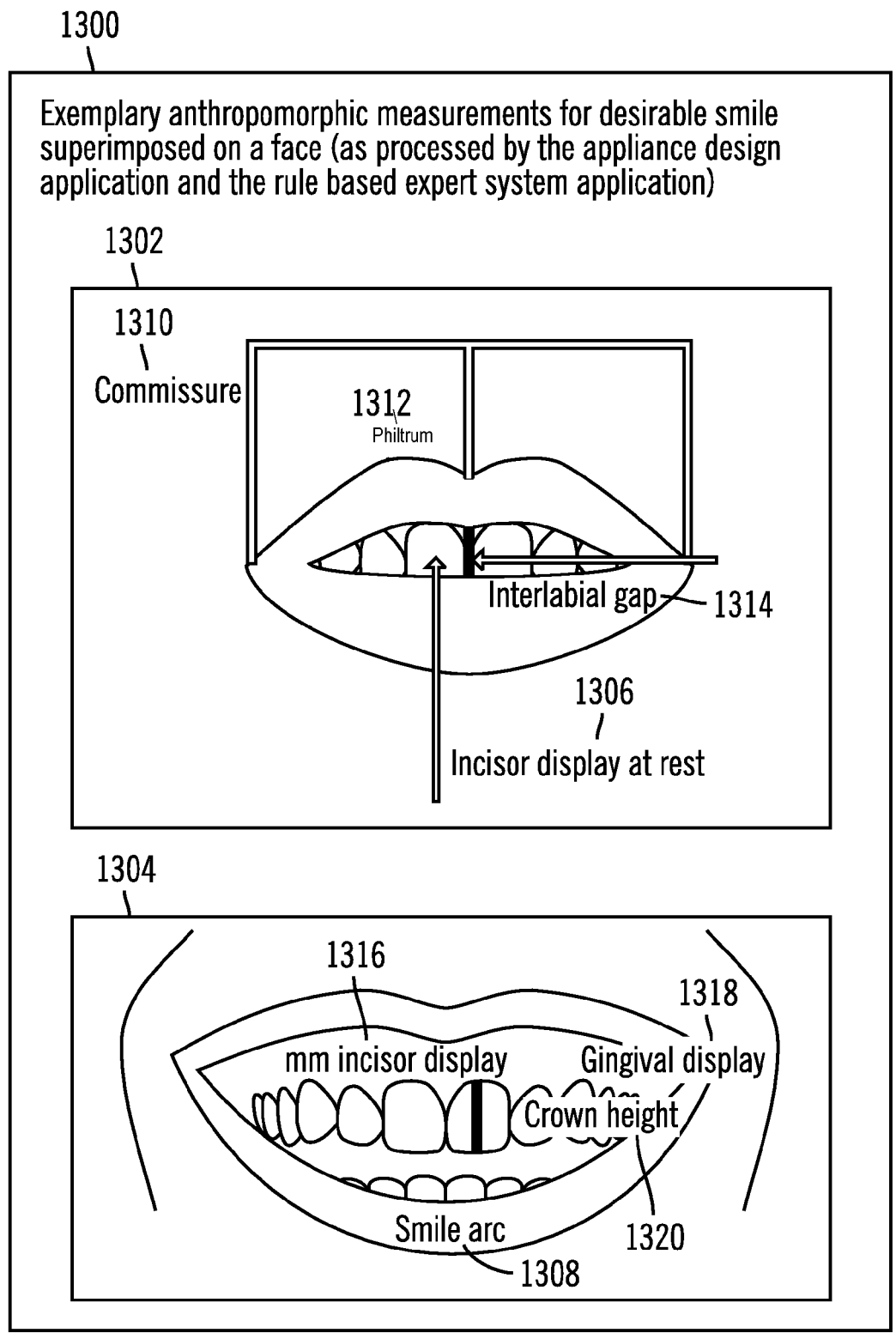
FIG. 13 illustrates a block diagram that shows exemplary anthropomorphic measurements for desirable smile superimposed on a face, as processed by the appliance design application and the rule based expert system application, in accordance with certain embodiments.

FIG. 13 illustrates a block diagram 1300 that shows exemplary anthropomorphic measurements for desirable smile superimposed on exemplary faces, as processed by the appliance design application 144 and the rule based expert system application 146, in accordance with certain embodiments.

Block 1302 shows exemplary incisor display at rest 1306, and block 1304 shows an exemplary smile arc 1308. In block 1302 exemplary dimensions related to the commissure 1310, the philtrum 1312, and the interlabial gap 1314 are shown. In block 1302 exemplary dimensions related to the millimeters of incisor display 1316, the gingival display 1318, and the crown height 1320 are shown.

Measurements related to the exemplary dimensions shown in FIG. 13 may be performed by identifying features in the digital imagery 114. For example, in certain embodiments, an image analysis software that is part of the appliance design application 144 or the rule based expert system application 146 may identify various features on photographs and images of a patient and determine the various dimensions.

Figure 14:
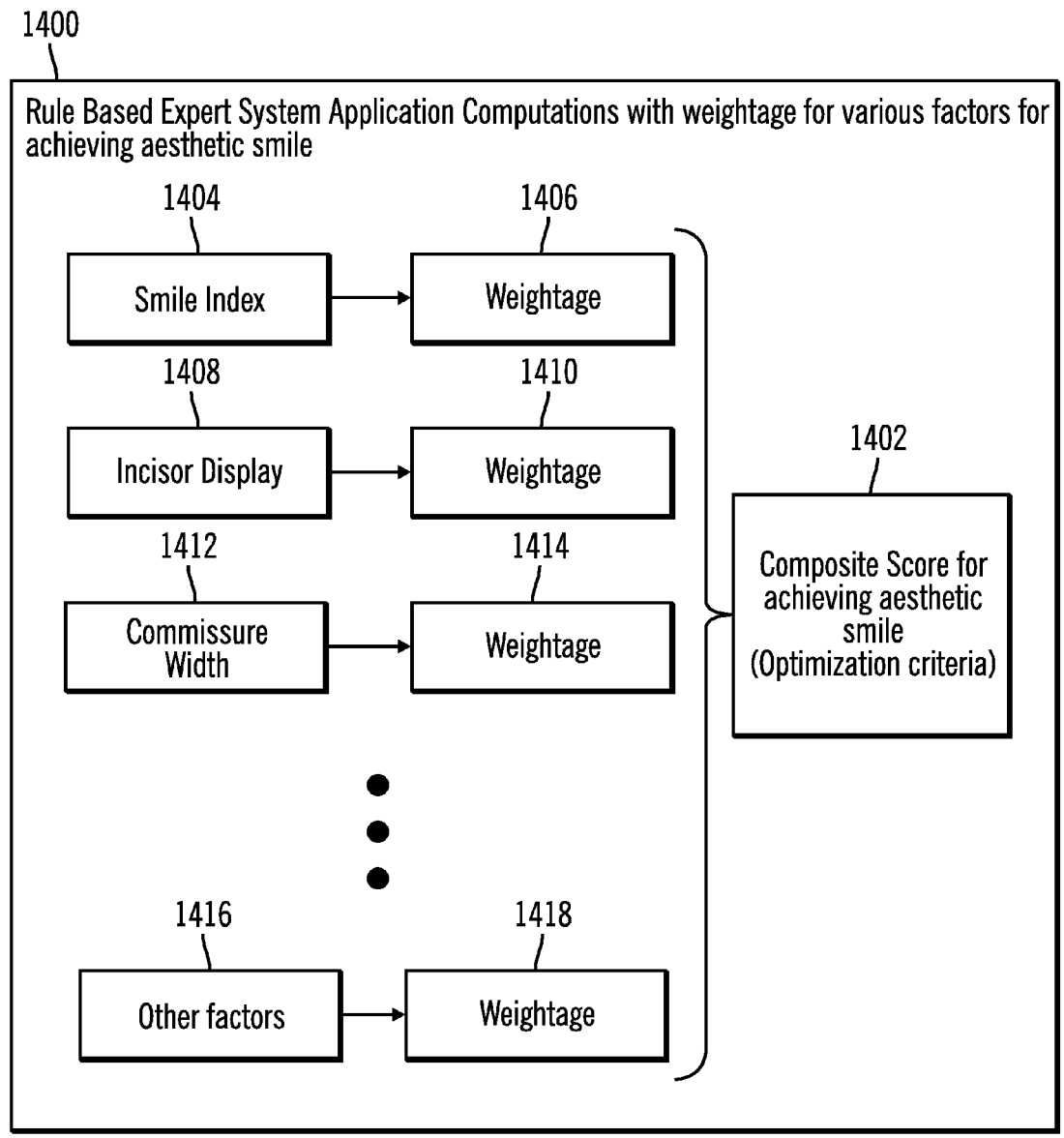
FIG. 14 illustrates a block diagram that shows exemplary computations performed by the rule based expert system application with weightage for various factors for achieving aesthetic smile, in accordance with certain embodiments.

FIG. 14 illustrates a block diagram 1400 that shows exemplary computations performed by the rule based expert system application 148 with weightage for various factors for achieving aesthetic smile, in accordance with certain embodiments.

In certain embodiments the rule base expert system application 146 may provide different weightages to different factors for arriving at a composite score 1402 that is optimized for achieving an aesthetic smile. The exemplary embodiment shown in FIG. 14 shows a weightage 1406 provided for the smile index 1404, a weightage 1410 provided for the incisor display 1408, a weightage 1414 provided for the commissure length 1412, and a weightage 1418 provided for other factors. In certain embodiments, the smile index 1404 may be weighted the most. It may not always be possible to optimize all the factors for achieving an aesthetic smile in a patient. Some factors may be weighted more and some may be weighted less. In certain embodiments, the composite score 1402 generated from the combination of the various factors is used to achieving an aesthetic smile. The operations for computing the composite score 1402 may be performed by the rule based expert system application 146 in combination with the appliance design application 144.

Figure 15:
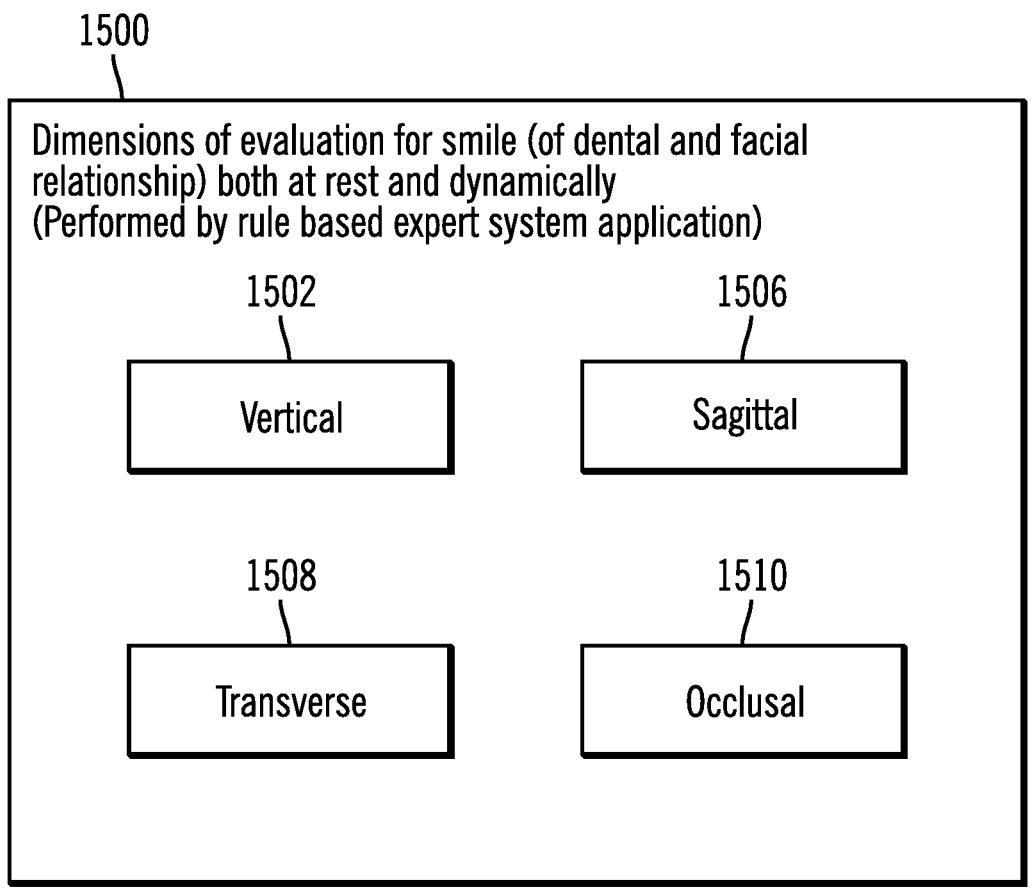
FIG. 15 illustrates a block diagram that shows exemplary dimensions for evaluation of smile performed by the rule based expert system application, in accordance with certain embodiments.

FIG. 15 illustrates a block diagram 1500 that shows exemplary dimensions for evaluation of smile performed by the rule based expert system application 146, in accordance with certain embodiments. In certain embodiments, the rule based expert system application 146 may perform analysis for achieving an aesthetic smile along the vertical 1502, sagittal 1506, transverse 1508, and occlusal 1510 dimensions.

Figure 16:
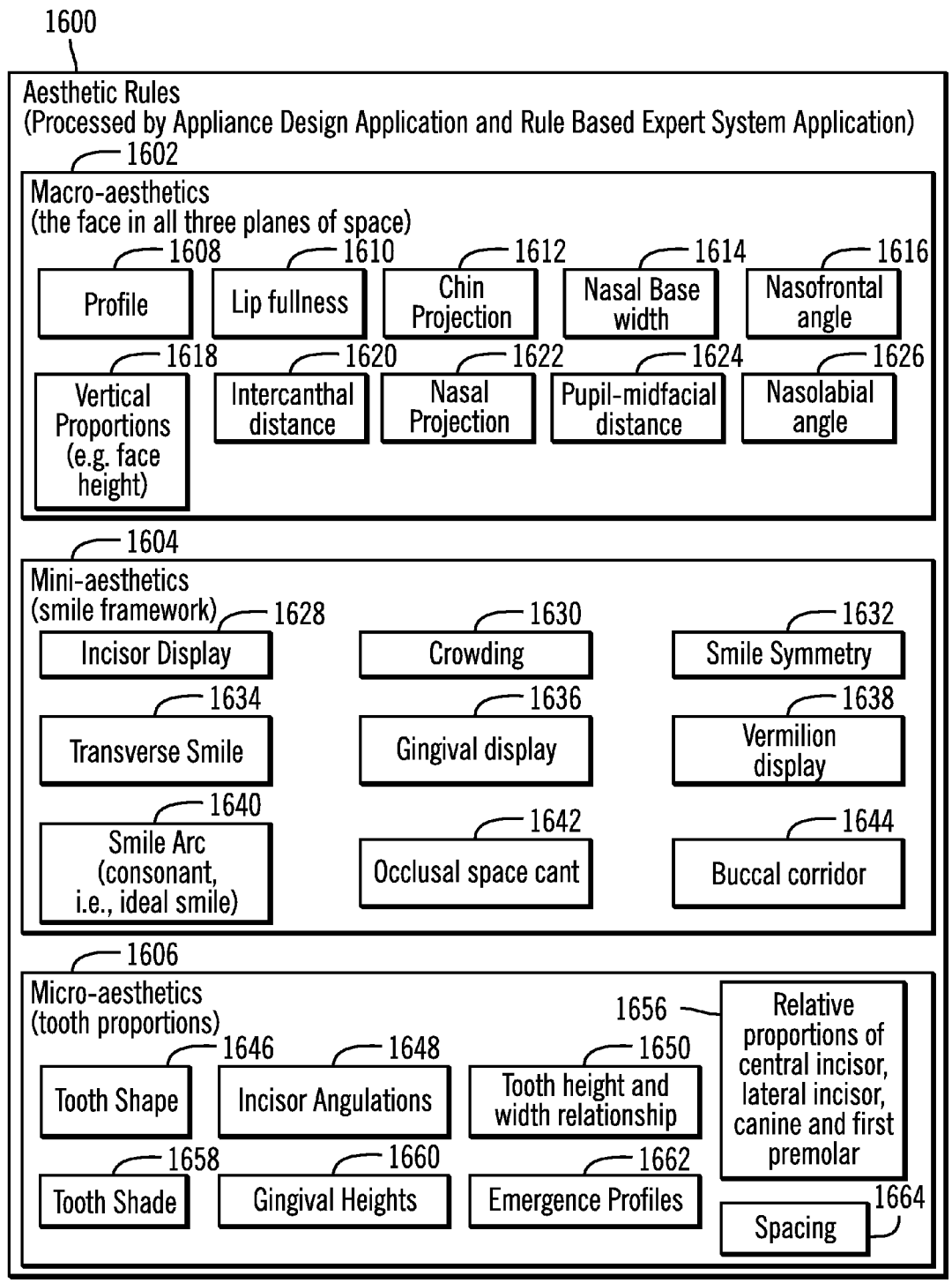
FIG. 16 illustrates a block diagram that shows exemplary macro-esthetics, mini-esthetics, and micro-esthetics rules processed by the appliance design application and the rule based expert system application, in accordance with certain embodiments.

FIG. 16 illustrates a block diagram 1600 that shows aesthetic rules including exemplary macro-esthetics 1602, mini-esthetics 1604, and micro-esthetics 1606 rules processed by the appliance design application 144 and the rule based expert system application 146, in accordance with certain embodiments.

The macro-aesthetics 1602 relate to aesthetics of the face in all three planes of space and may include for a patient the profile 1608, the lip fullness 1610, the chin projection 1612, the nasal base width 1614, the nasofrontal angle 1616, the vertical proportions such as the face height 1618, the intercanthal distance 1620, the nasal projection 1622, the pupil-midfacial distance 1624, the nasolabial angle 1626, etc.

The mini-aesthetics 1604 are related to the smile framework and may include factors such as incisor display 1628, crowding of teeth 1630, smile symmetry 1630, transverse smile 1634, gingival display 1636, vermilion display 1638, smile art 1640, occlusal space cant 1642, buccal corridor 1644, etc.

The micro-aesthetics 1605 are related to the tooth proportions and may include factors such as tooth shape 1646, incisor angulations 1648, tooth height and width relationship 1650, relative proportions of central incisor, lateral incisor, canine and first premolar 1656, tooth shade 1658, gingival heights 1650, emergence profiles 1662, spacing 1664, etc.

In designing an orthodontic appliance for achieving an aesthetic smile some of all of the factors for macro-aesthetics 1602, mini-aesthetics 1604, and micro-aesthetics 1606 may be considered by the appliance design application 144 and the rule based expert system application 148.

Figure 17:
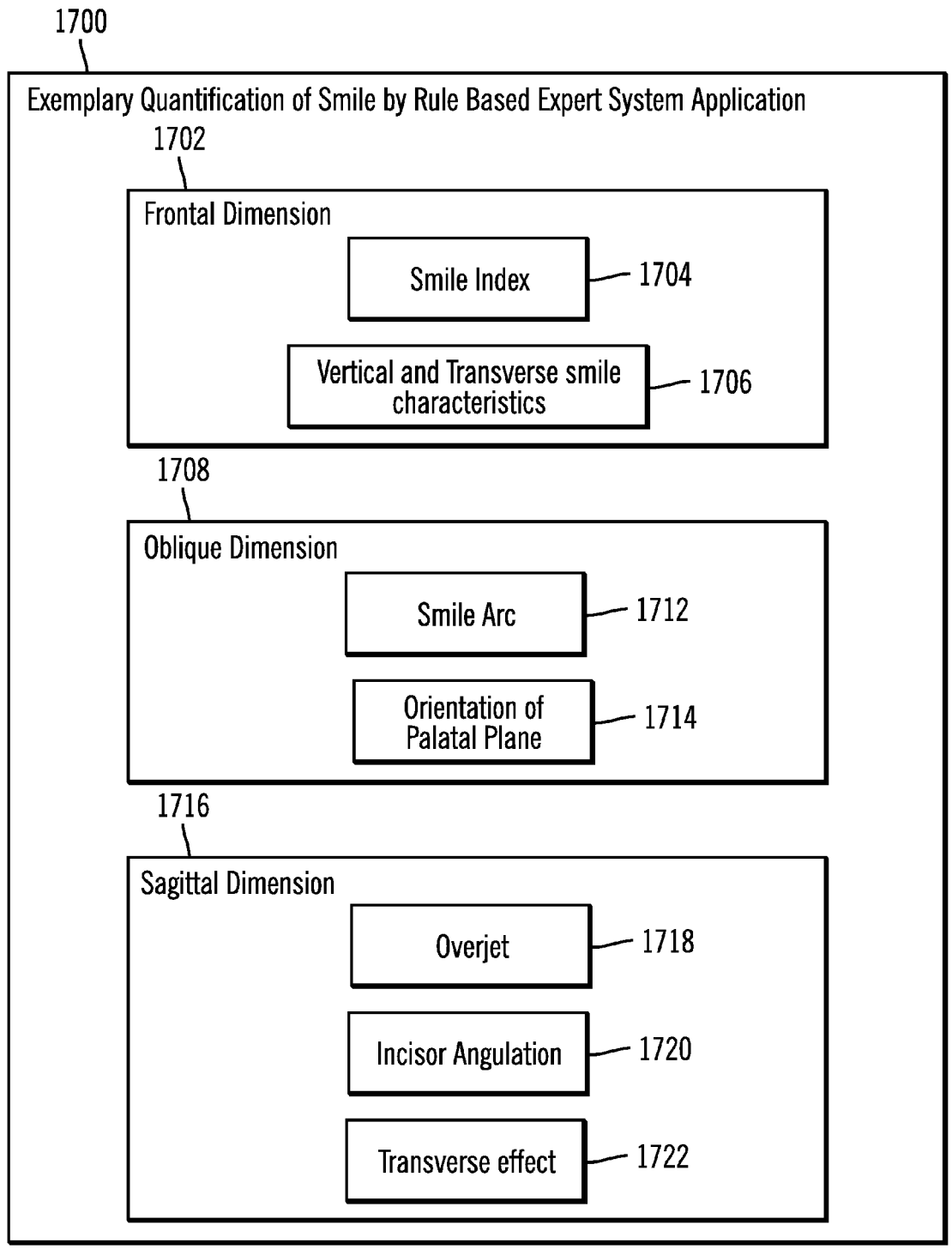
FIG. 17 illustrates a block diagram that shows an exemplary quantification of smile by the rule based expert system application, in accordance with certain embodiments.

FIG. 17 illustrates a block diagram 1700 that shows an exemplary quantification of smile by the rule based expert system application 148, in accordance with certain embodiments.

In the fontal dimension 1702 the smile index 1704 and the vertical and transverse smile characteristics 1706 are considered. In the oblique dimension 1704 the smile arc 1712 and the orientation of the palatal plane 1714 are considered. In the sagittal dimension 1716 the overjet 1718, the incisor angulation 1720, and the transverse effect 1722 are considered.

The quantification of the smile that is desired on a patient may lead to the appliance design application 144 in combination with the rule based expert system application 146 to design a suitable appliance to achieve an aesthetic smile for the patient.

Figure 18:
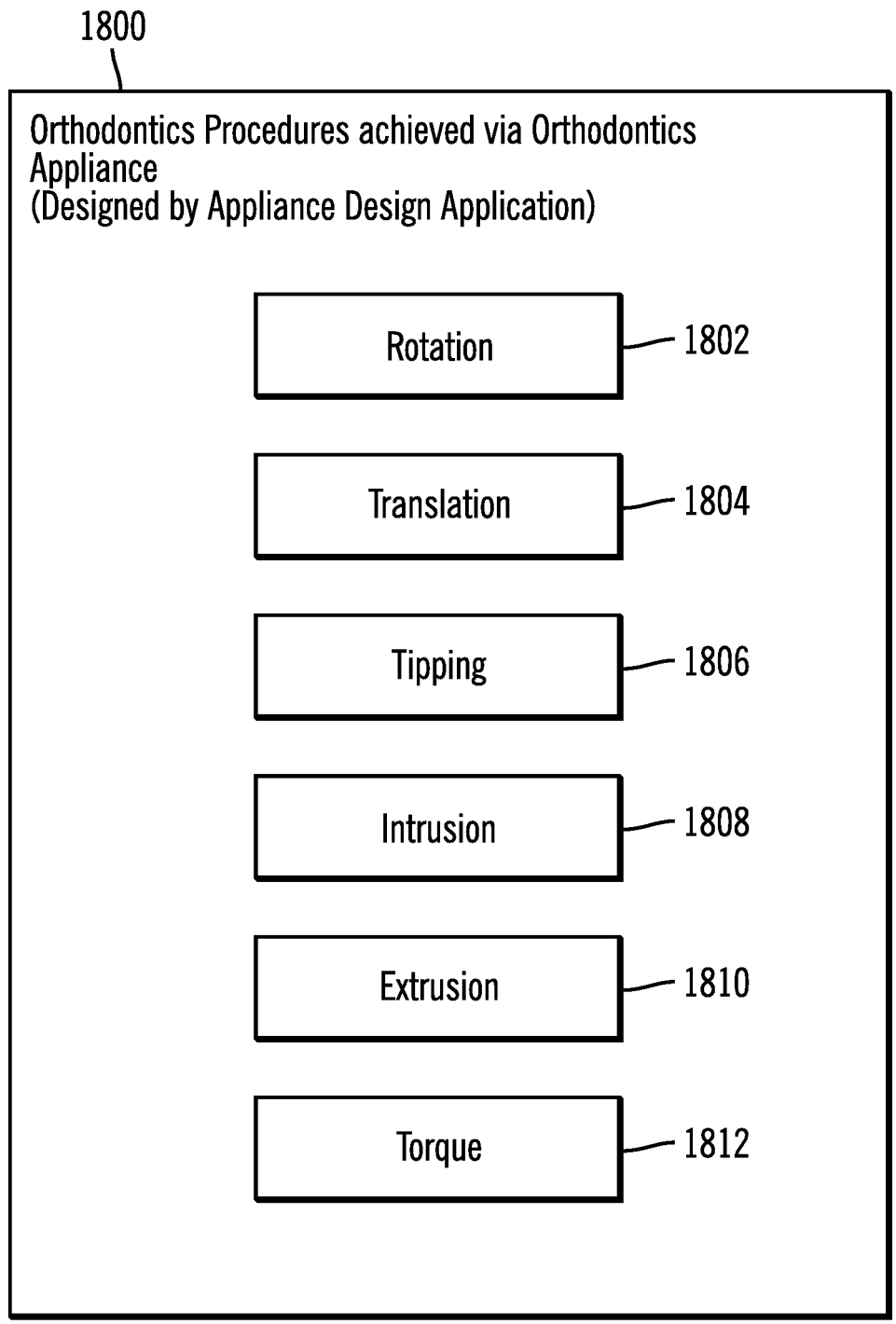
FIG. 18 illustrates a block diagram that shows orthodontics procedures achieved via an orthodontic appliance designed by the appliance design application, in accordance with certain embodiments.

FIG. 18 illustrates a block diagram 1800 that shows orthodontics procedures achieved via an orthodontic appliance designed by the appliance design application 144, in accordance with certain embodiments. The orthodontic procedures that may be achieved may include rotation 1802, translation 1804, tipping 1806, intrusion 1808, extrusion 1810, and torque 1812. Such orthodontics procedures may be applied in the orthodontic appliance to achieve an aesthetic smile.

Figure 19:
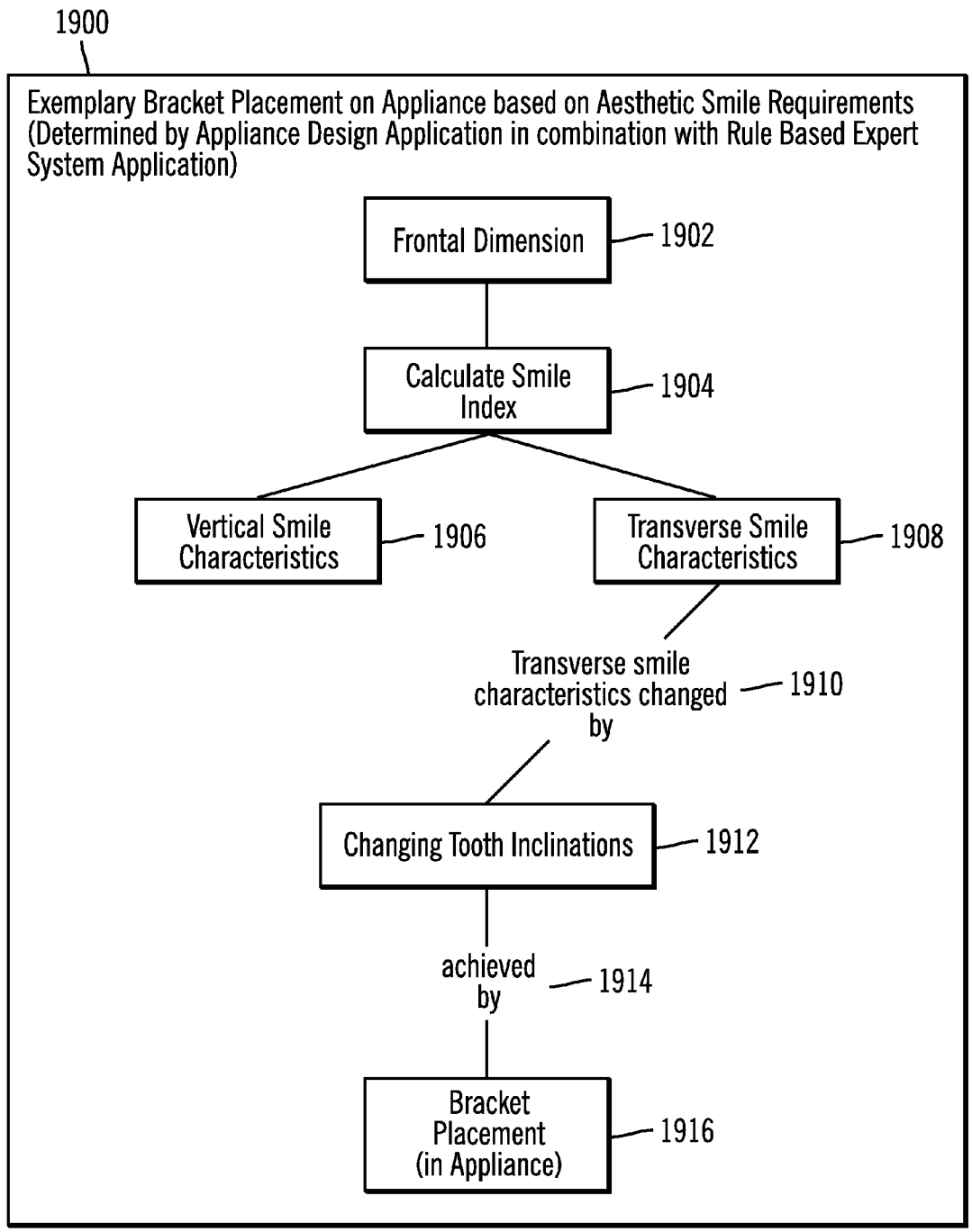
FIG. 19 illustrates a block diagram that shows exemplary bracket placement based on aesthetic smile requirements determined by the appliance design application in combination with the rule based expert system application, in accordance with certain embodiments.

FIG. 19 illustrates a block diagram 1900 that shows exemplary bracket placement based on aesthetic smile requirements determined by the appliance design application 144 in combination with the rule based expert system application 148, in accordance with certain embodiments.

In certain embodiments, based on the frontal dimensions 1902 of a patient, a smile index may be calculated. The smile index may be related to vertical smile characteristics 1906 and transverse smile characteristics 1908. FIG. 19 shows that in certain embodiments the transverse smile characteristics are changed (reference numeral 1910) by changing tooth inclinations that are achieved by (reference numeral 1914) bracket placements 1916 in an appliance. The bracket placements are determined by the appliance design application 144.

Figure 20:
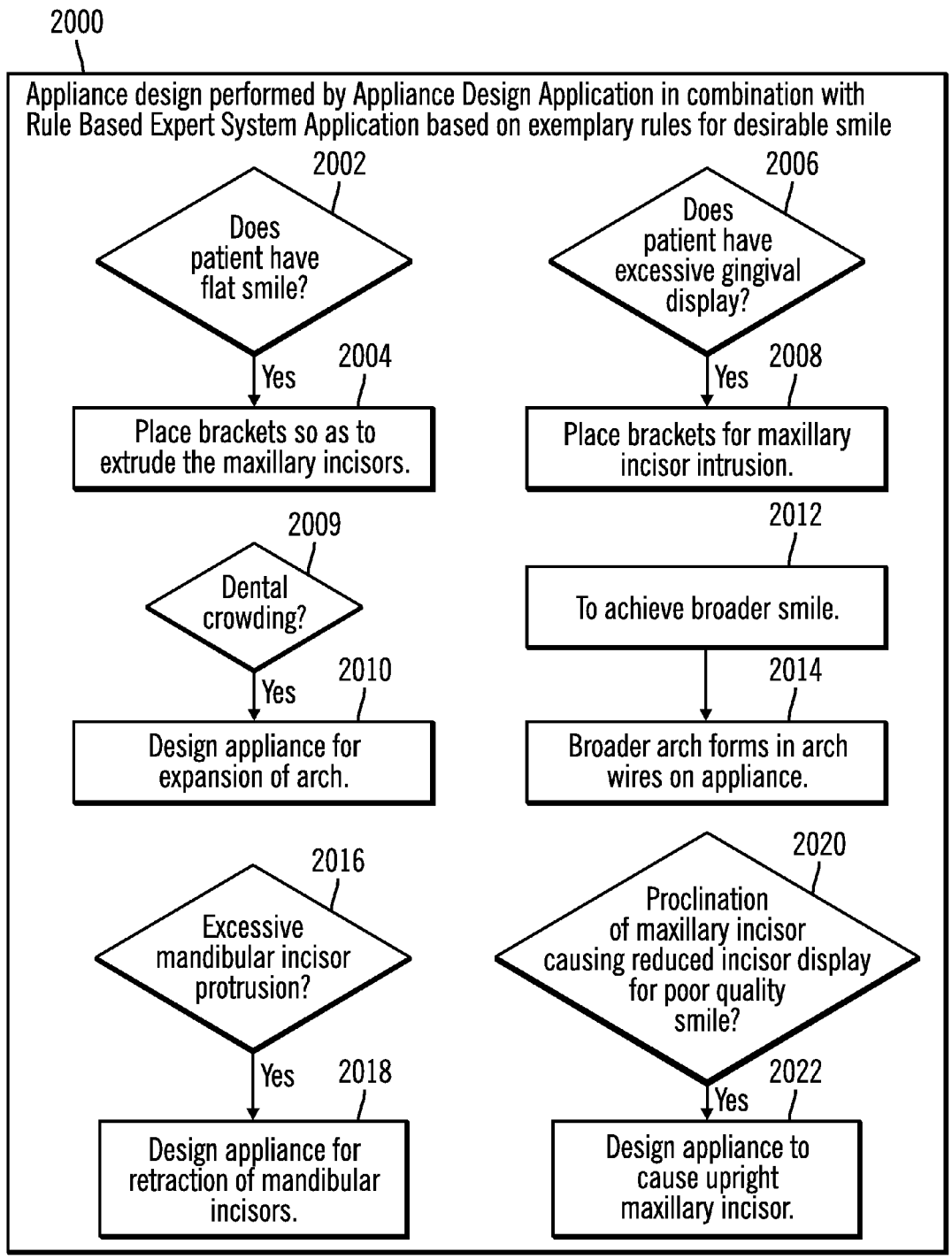
FIG. 20 illustrates a block diagram that shows exemplary appliance design performed by the appliance design application in combination with the rule based expert system application based on aesthetic smile requirements, in accordance with certain embodiments.

FIG. 20 illustrates a block diagram 2000 that shows exemplary appliance design performed by the appliance design application 144 in combination with the rule based expert system application 146 based on aesthetic smile requirements, in accordance with certain embodiments.

In one embodiment, if a determination is made by the rule based expert system application 146 that the patient has a flat smile 2002, then the appliance design application 144 may design the orthodontic appliance to place brackets so as to extrude the maxillary incisors 2004.

In another embodiment, if a determination is made by the rule based expert system application 146 that the patient has excessive gingival display 2006, then the appliance design application 144 may design the orthodontic appliance to place brackets for maxillary incisor intrusion 2008.

In another embodiment, if a determination is made by the rule based expert system application 146 that the patient has dental crowding 2009, then the appliance design application 144 may design the orthodontic appliance to place brackets for expansion of arch 2010.

In another embodiment, if a determination is made by the rule based expert system application 146 that the patient needs to achieve a broader smile 2012, then the appliance design application 144 may design the orthodontic appliance such that broader arch forms are present in arch wires of the orthodontic appliance 2014.

In another embodiment, if a determination is made by the rule based expert system application 146 that the patient has excessive mandibular incisor protrusion 2016, then the appliance design application 144 may design the orthodontic appliance to place brackets for retraction of the mandibular incisors 2018.

In another embodiment, if a determination is made by the rule based expert system application 146 that the patient has a proclination of maxillary incisor that caused reduced incisor display resulting in a poor quality smile 2020, then the appliance design application 144 may design the orthodontic appliance to place brackets so as to cause an upright maxillary incisor 2022.

It may be noted that the embodiments provided in FIG. 20 are exemplary in nature and other embodiments may be employed to achieve an aesthetic smile.

Figure 21:
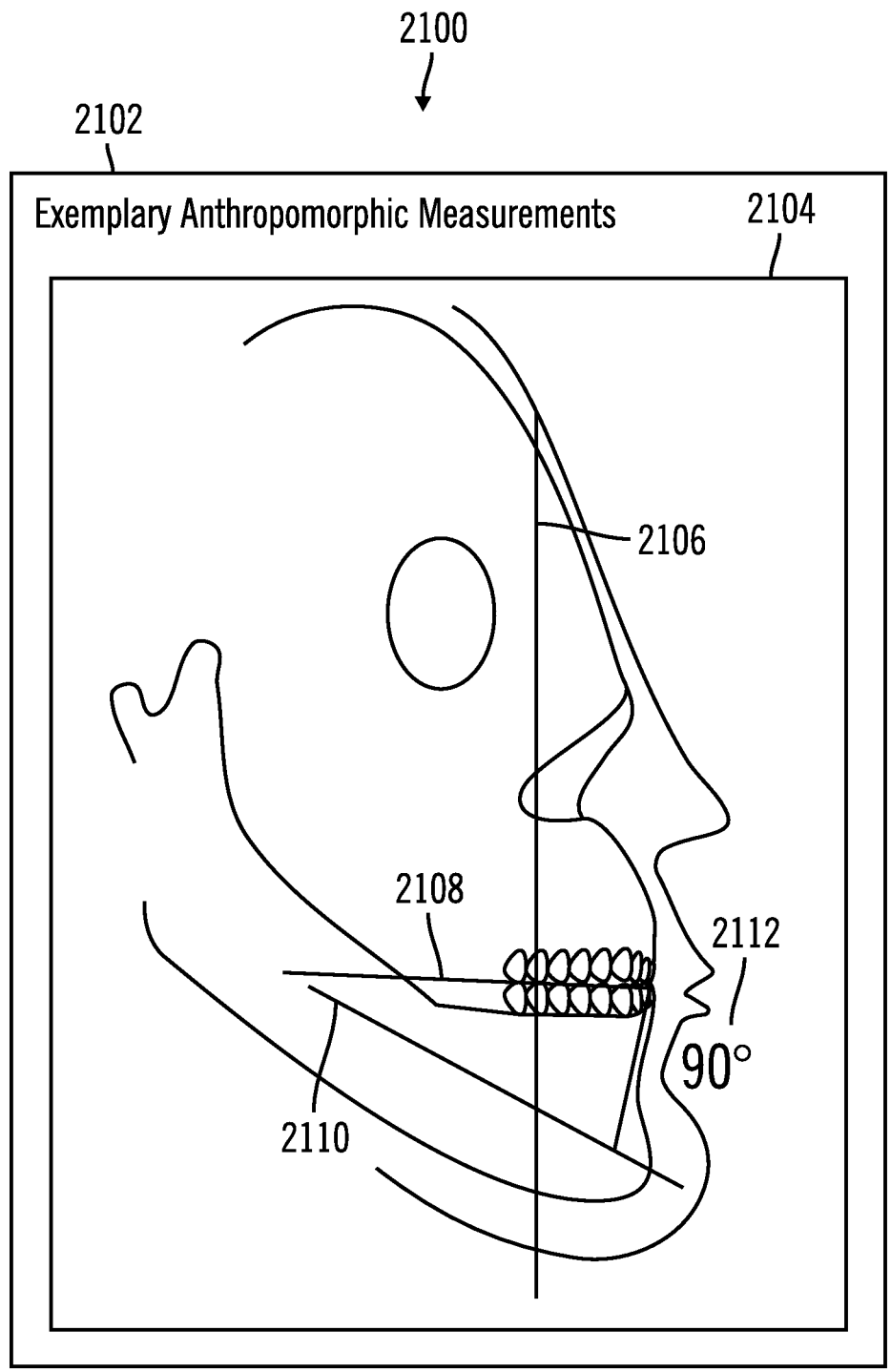
FIG. 21 illustrates a block diagram that shows exemplary anthropomorphic dimensions as determined by the appliance design application in combination with the rule based expert system application, in accordance with certain embodiments

FIG. 21 illustrates a block diagram 2100 that shows exemplary anthropomorphic measurements 2102, in accordance with certain embodiments. The image 2104 shown in FIG. 21 may be received by the appliance design computational device 102 from the clinic site device 104 via the digital imagery 114 that is sent over the network 106. Various lengths, segments, and positions 2106, 2108, 2110 and angles 2112 may be measured via analysis of the image 2104 by the rule based expert system application 146 and the computed values entered in the corresponding anthropomorphic measurements 150. In certain embodiments, the exemplary anthropomorphic measurements 2102 from the clinic site device 104 may comprise numeric values modeling the measurements. Alternatively, the exemplary anthropomorphic measurements 2102 may comprise an image which is analyzed by an imaging device and program at the appliance design computational device 102 to produce numerical measurements that may be processed the rule based expert system application 146 for analysis.

Figure 22:
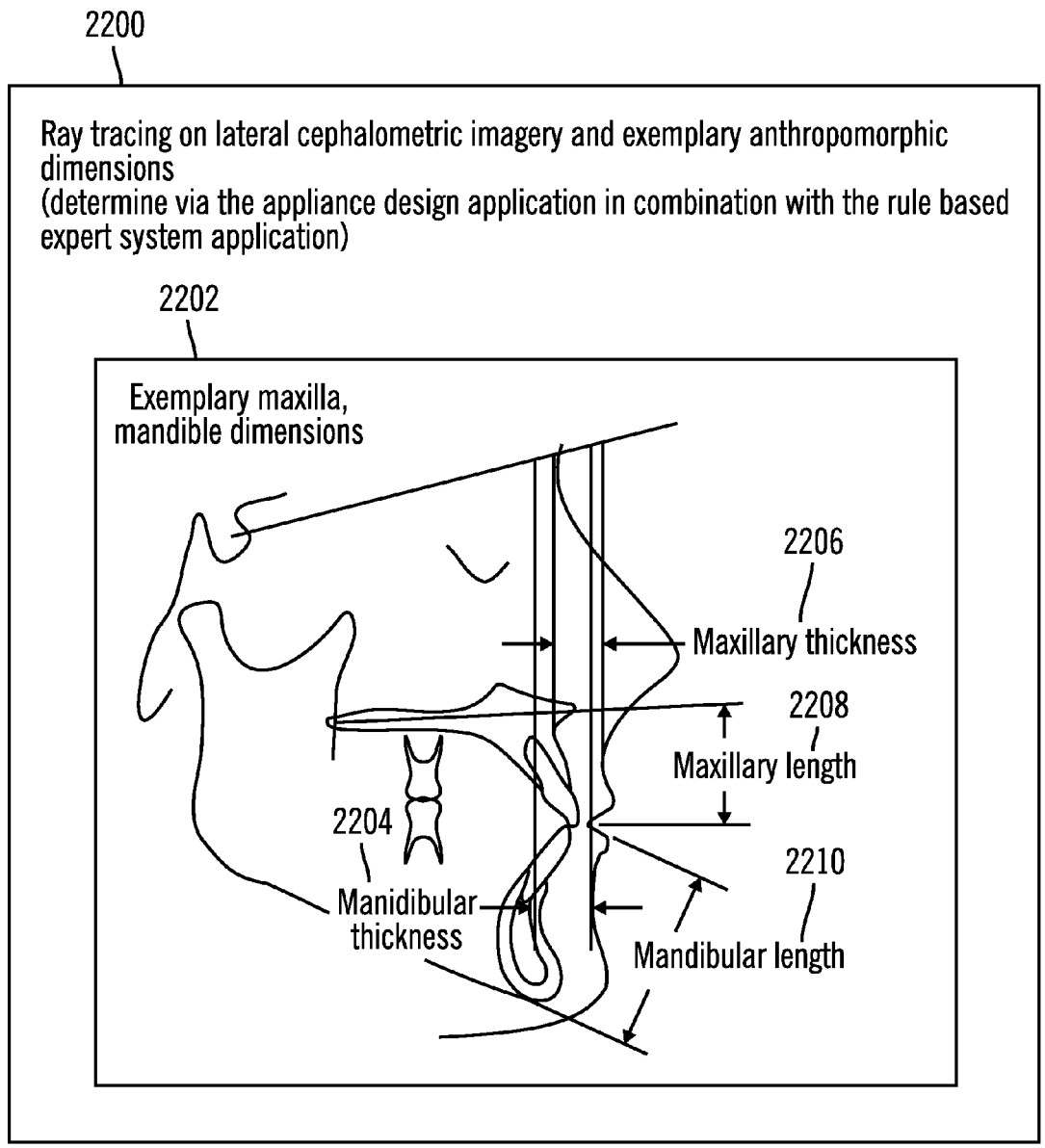
FIG. 22 illustrates a block diagram that shows ray tracing on lateral cephalometric imagery and exemplary anthropomorphic dimensions as determined by the appliance design application in combination with the rule based expert system application, in accordance with certain embodiments.

FIG. 22 illustrates a block diagram 2200 that shows ray tracing on lateral cephalometric imagery and exemplary anthropomorphic dimensions as determined by the appliance design application 144 in combination with the rule based expert system application 146, in accordance with certain embodiments. The dimensions may be generated via ray tracing on lateral cephalometric imagery that may be included in the digital imagery 114. Exemplary maxilla and mandible dimensions 2202 shown in FIG. 22 includes the mandibular thickness 2204, the maxillary thickness 2206, the maxillary length 2208, and the mandibular length 2210, These measurements may be used by the appliance design application 144 in combination with the rule based expert system application 146 to generate an aesthetic smile.

Figure 23:
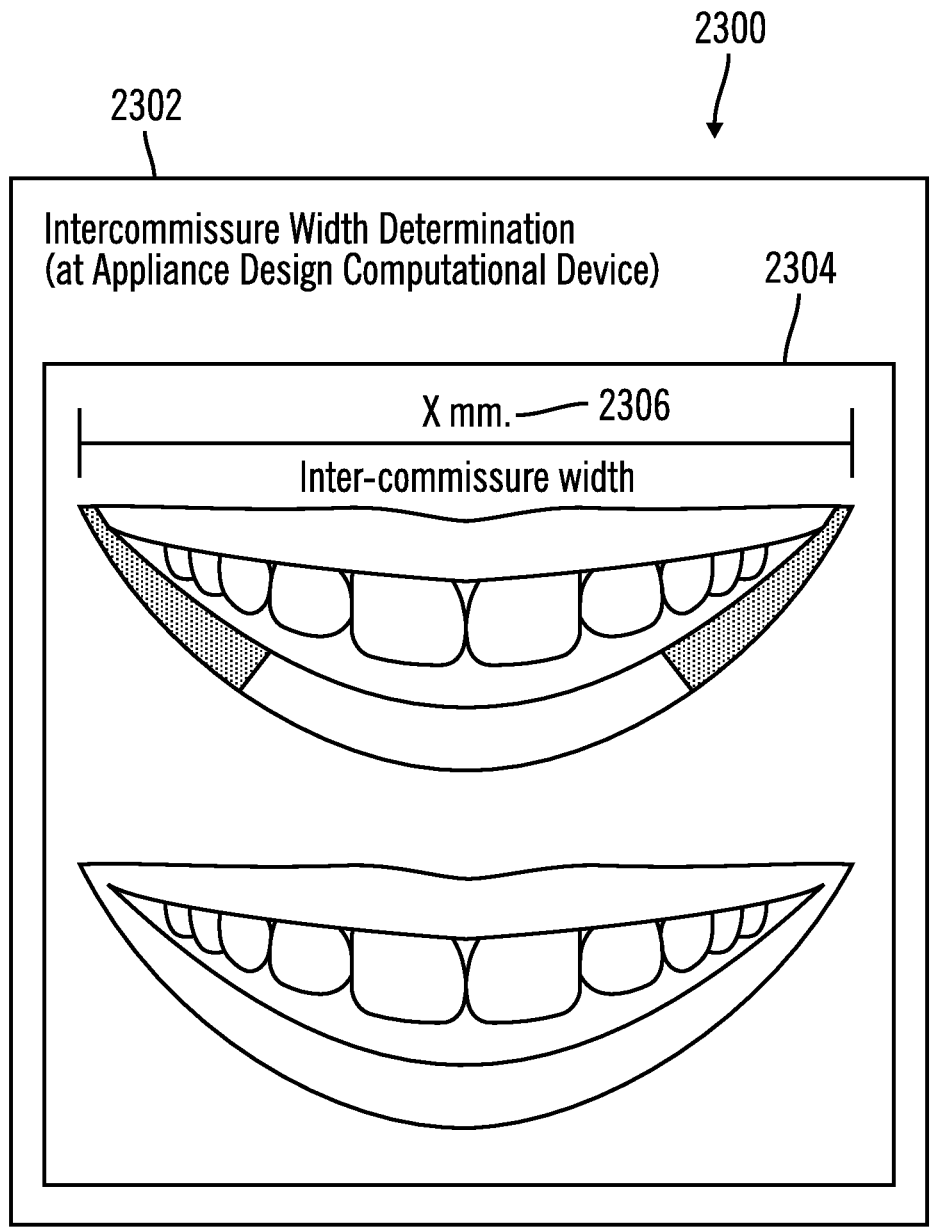
FIG. 23 illustrates a block diagram that shows exemplary inter-commissure width determination, in accordance with certain embodiments.

FIG. 23 illustrates a block diagram 2300 that shows certain embodiments for exemplary inter-commissure width determination 2302. The commissure is the corner of the mouth, where the vermillion border of the superior labium (upper lip) meets that of the inferior labium (lower lip). The commissure is important in facial appearance, particularly during function such as smiling. The inter-commissure width is the distance between the two commissures of the mouth. To visualize and quantify the frontal smile ratio, a smile index that describes the area framed by the vermilion borders of the lips during the social smile is defined. The smile index is determined by dividing the inter-commissure width by the interlabial gap during smile. The interlabial gap is the distance between the upper and lower lips. This ratio is helpful for comparing smiles among different patients or across time in one patient.

The image 2304 shown in FIG. 23 may have been generated by the rule based expert system application 146 from dental imagery 134 received over the network 106. The rule based expert system application 146 may determine line, areas, objects, etc., via image analysis and application of computer vision techniques. The inter-commissure width dimension 2306 is measured in the image 2304 by locating the corners of lips and measuring the distance as shown. The inter-commissure width dimension 2306 is entered into the inter-commissure width data structure 1002 by the rule based expert system application 146.

Figure 24:
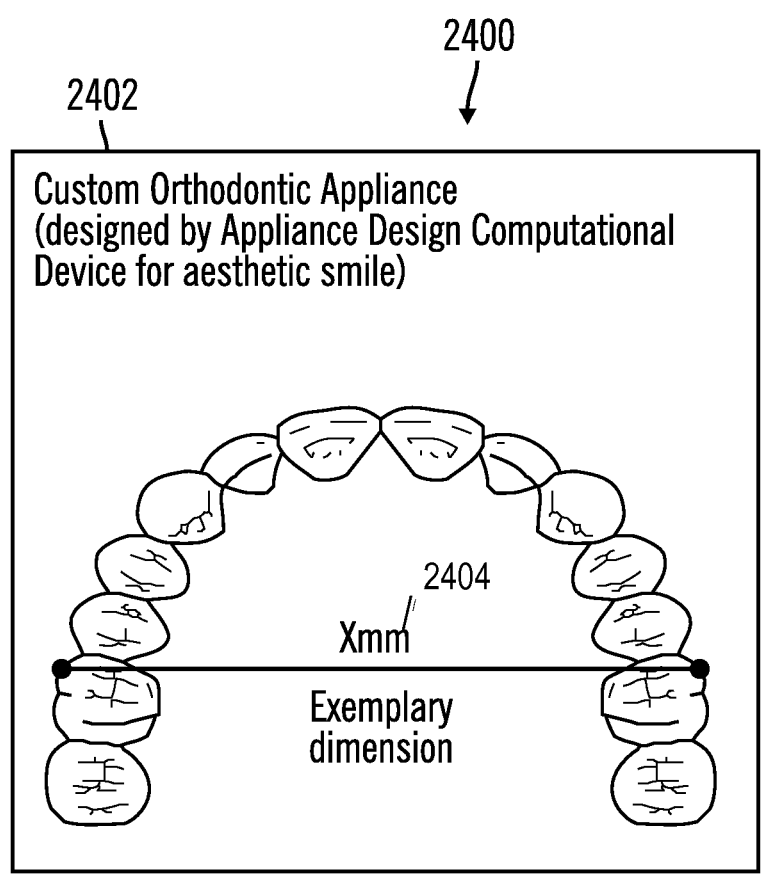
FIG. 24 illustrates a block diagram that shows an exemplary custom orthodontic appliance, in accordance with certain embodiments.

FIG. 24 illustrates a block diagram 2400 that shows the design of an exemplary custom orthodontic appliance 2402, in accordance with certain embodiments. The custom orthodontic appliance 2402 has a dimension 2404 that is identical to the inter-commissure width 1002 shown in FIG. 10 for providing an optimum smile in accordance with the rule on aesthetic smile 1016.

Figure 25:
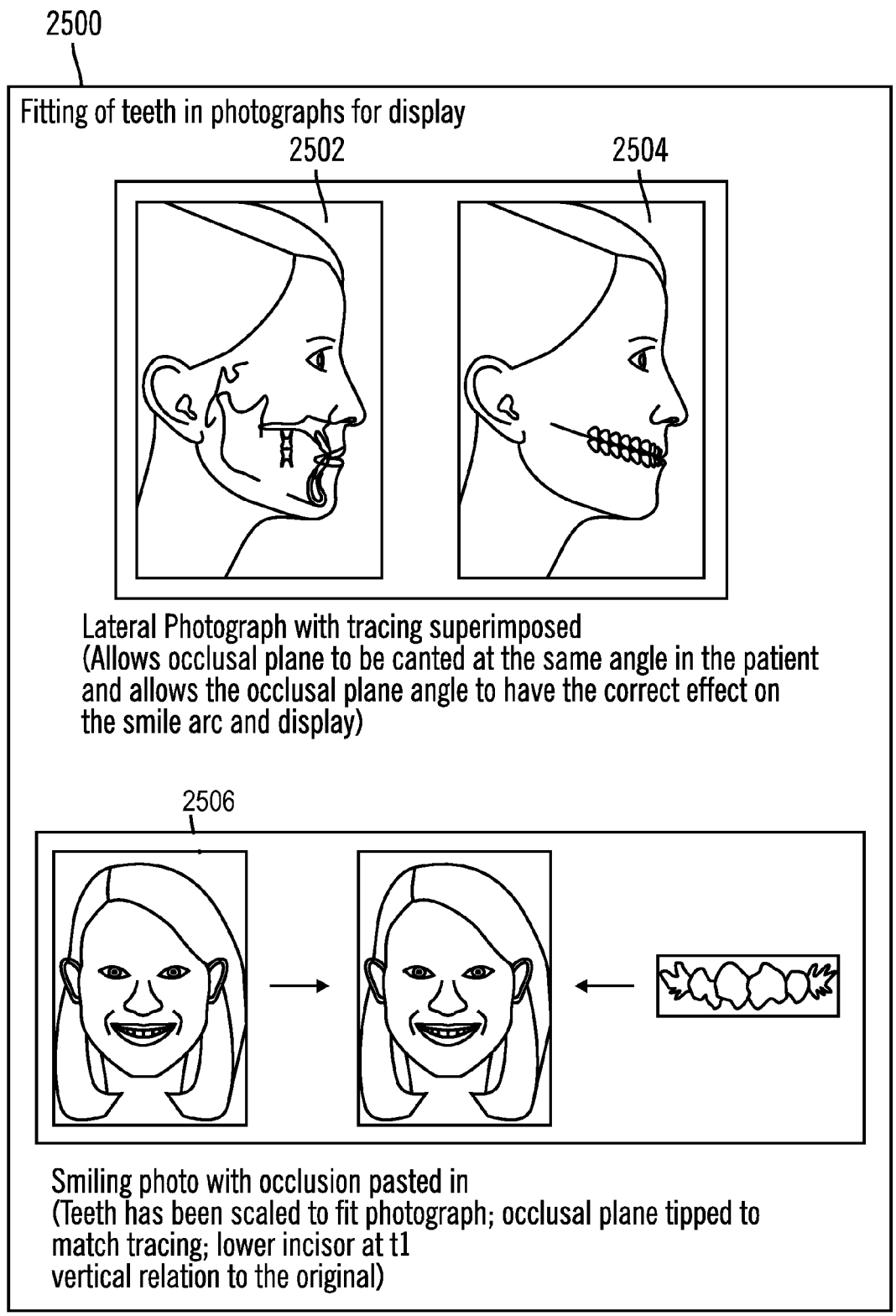
FIG. 25 illustrates a block diagram that shows how teeth are fitted in a photograph, in accordance with certain embodiments.

FIG. 25 illustrates a block diagram 2500 that shows how teeth are fitted in a photograph, in accordance with certain embodiments. The photograph may be sent as digital imagery 114 from the clinic site device 104 to the appliance design computational device 102. In certain embodiments, tracing may be superimposed on a lateral photograph of a patient (reference numeral 2502). The occlusal plane is shown to be canted at the same angle in the patient and this allows the occlusal plane angle to have the correct effect on the smile arc and display (reference numeral 2504). Furthermore, the appliance design application 144 in combination with the rule based expert system application 148 may send a smiling photograph as a digital model of patient smile 184 with occlusion pasted in (as shown via reference numeral 2506). The smiling photograph may be stored as an exemplary simulated smile display for the patient (reference numeral 166 in FIG. 1) and displayed to the patient.

Figure 26:
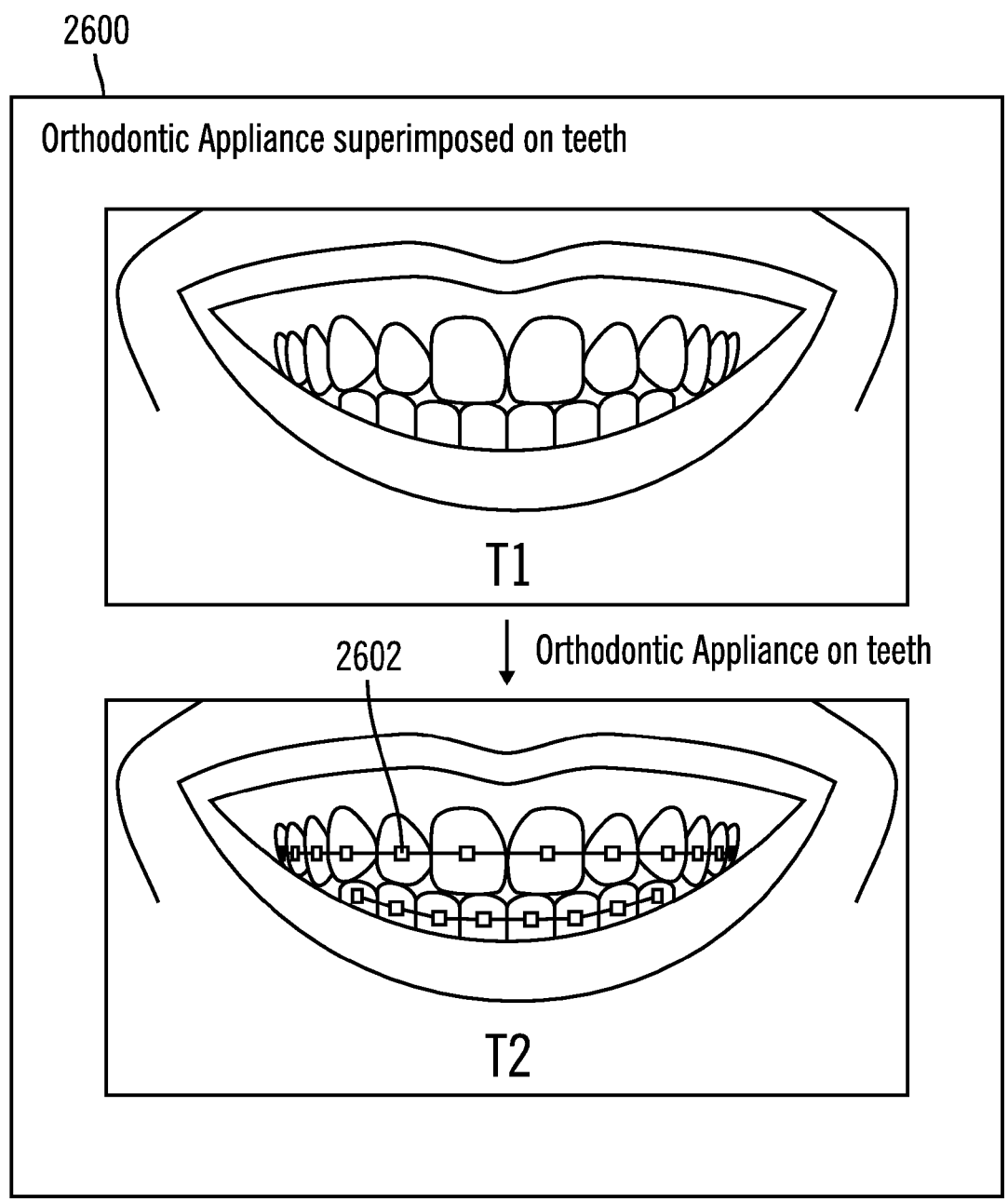
FIG. 26 illustrates a block diagram that shows an orthodontic appliance superimposed on teeth in, in accordance with certain embodiments.

FIG. 26 illustrates a block diagram 2600 that shows an orthodontic appliance 2602 superimposed on teeth, in accordance with certain embodiments. The generation of the superimposition of the orthodontic appliance on teeth may be performed by the appliance design application 144 in combination with the rule based expert system application 146, and a digital image of the superimposed orthodontic appliance on the teeth may be transmitted to the clinic site device 104 for display to the patient.

Figure 27:
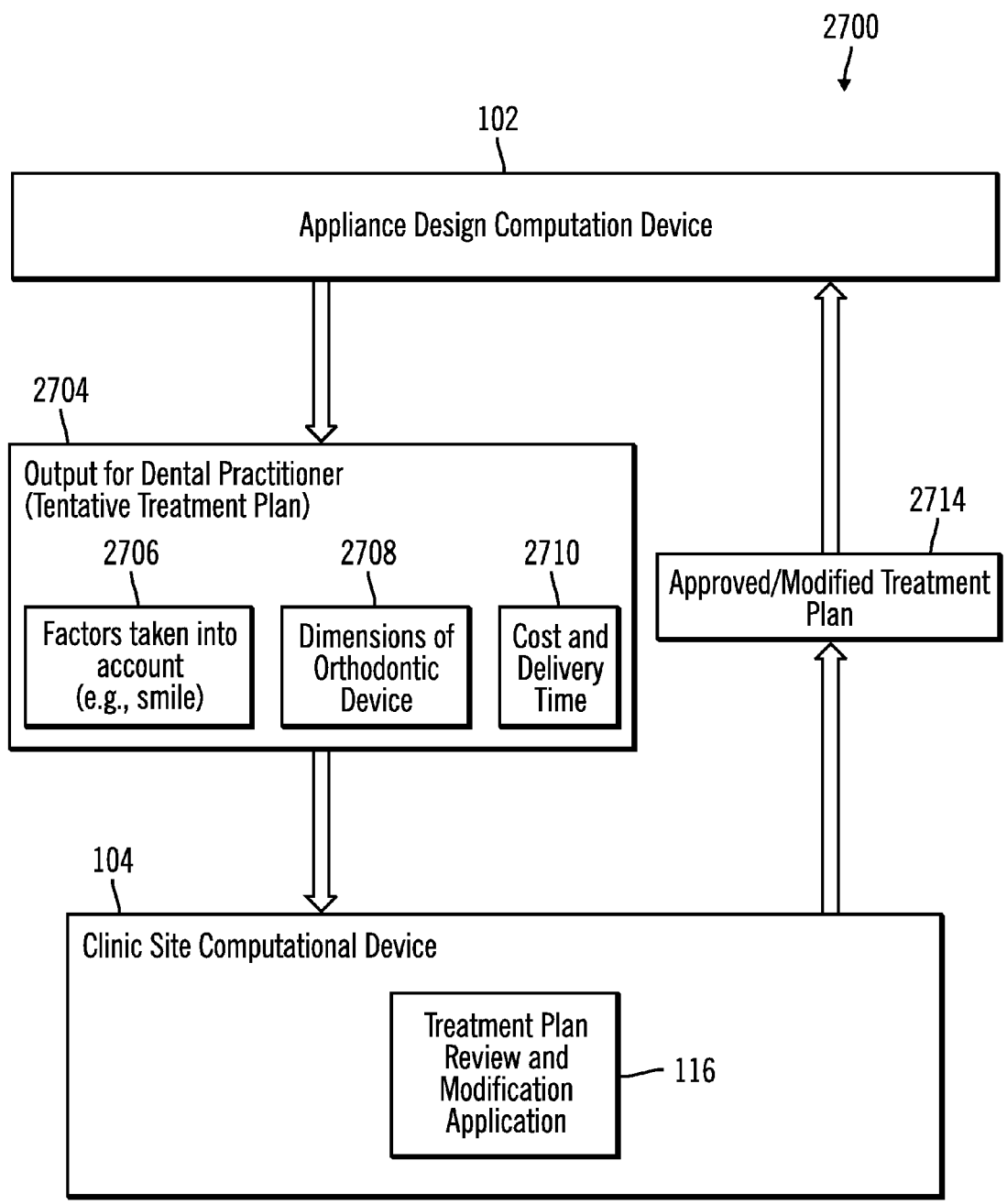
FIG. 27 illustrates a block diagram that shows interactions with respect to treatment plans between an appliance design computational device and a clinic site device, in accordance with certain embodiments.

FIG. 27 illustrates a block diagram 2700 that shows interactions with respect to treatment plans between an appliance design computational device 102 and a clinic site device 104, in accordance with certain embodiments.

The appliance design computational device 102 may generate an output 2704 for the dental practitioner based on analysis of the dental imagery 114 and application of the rules 148 and anthropomorphic measurements 150 in association with the rule based expert system application 146 and the appliance design application 144. The output 2704 may comprise a suggested tentative treatment plan. The output 2704 takes into consideration the design aspect of appliance design and the rules 148 maintained at the appliance design computational device 102.

The output for the orthodontist 2704 indicates factors taken into account (e.g., smile) 2706 while designing the orthodontic appliance, the dimensions 2708 of the orthodontic appliance, and optionally the cost and delivery time 2710.

The suggested treatment plan may comprise a prescription that includes the characteristics, such as dimensions, orientations, etc., of some of the elements (e.g., archwire, slots) that comprise a tentative design of the orthodontic appliance. An exemplary orthodontic appliance may comprise an orthodontic brace. Values of torque, angulation and rotation of elements of the orthodontic brace may form part of the prescription. In alternative embodiments, the suggested treatment plan may include prescriptions for other orthodontic devices besides orthodontic braces. It may be noted that orthodontic treatment is based on the principle that is pressure is applied to a tooth then tooth movement occurs as the bone around the tooth remodels. For example, application of a single force to a crown of a tooth may create a rotation around a point about halfway down to the root. Also, if two forces are applied simultaneously to a tooth the tooth may be translated over time. The application of braces moves the teeth as a result of force and pressure on the teeth. There are four basic elements that are needed in order to help move the teeth. In the case of traditional metal or wire braces, certain systems use brackets, bonding material, arch wire, and ligature elastic, to help align the teeth. The teeth may move when the arch wire puts pressure on the brackets and teeth. Sometimes springs or rubber bands are used to put more force in specific directions. Braces have constant pressure, which over time, move teeth into their proper positions.

The clinic site device 104 receives the output 2704 that includes the tentative treatment plan 2704 and sends an electronic notification to the dental practitioner to review the tentative treatment plan 1704. The dental practitioner may approve the tentative treatment plan via the treatment plan review and modification application 116. If the dental practitioner is not satisfied, then the dental practitioner may use the treatment plan review and modification application 116 to send a modified treatment plan 2714 to the appliance design computational device 102. The appliance design computational device 102 may design the custom orthodontic appliance based on the modified treatment plan 2714 or the approved the treatment plan. Additional rounds of interaction may take place between the appliance design computational device 102 and the clinic site device 104 to arrive at further refinements to the treatment plan. It should be noted that responsibility for the final approval of the treatment plan rests with the dental practitioner at the clinic site 110.

Figure 28:
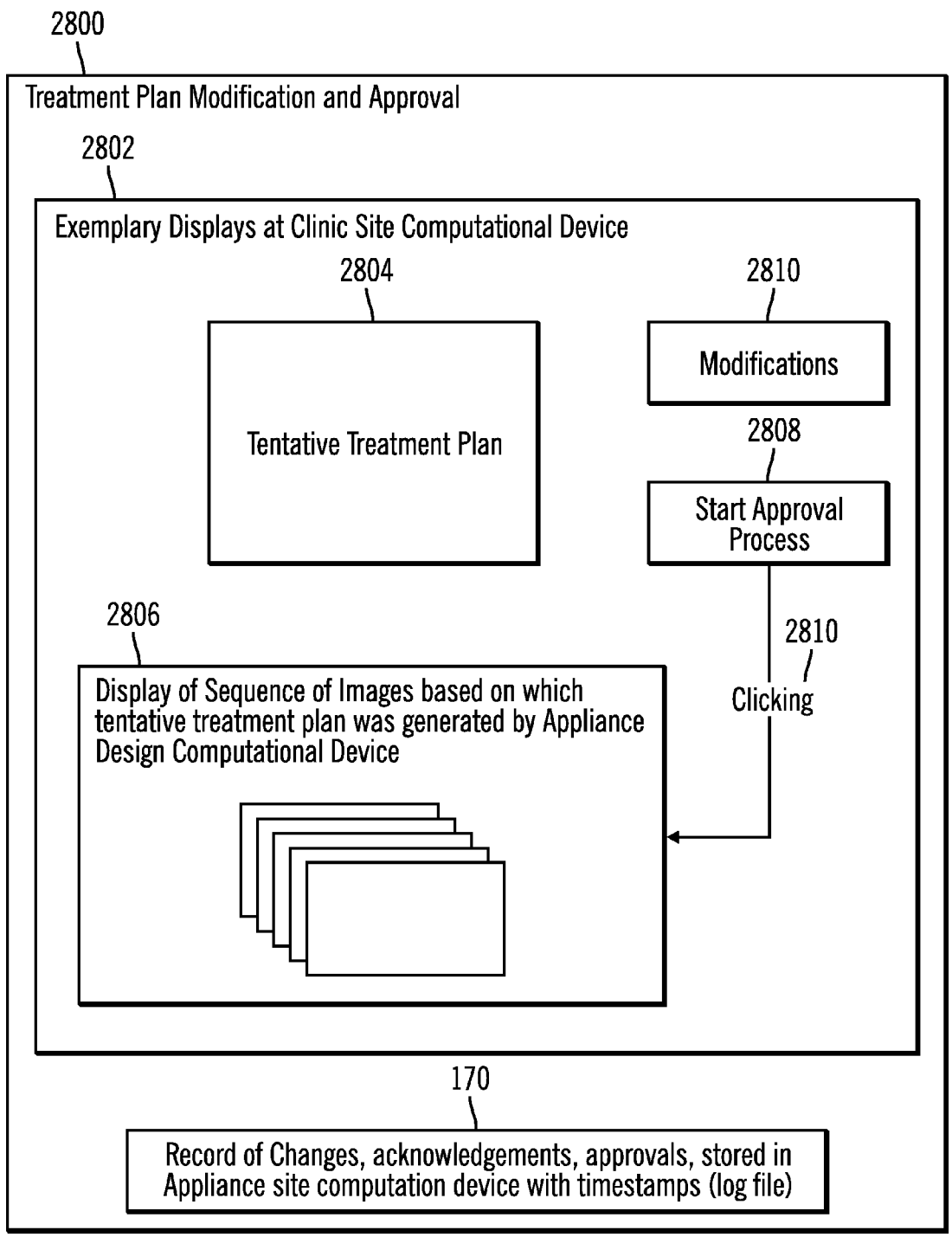
FIG. 28 illustrates a block diagram that shows additional interactions with respect to treatment plans between an appliance design computational device and a clinic site device, in accordance with certain embodiments.

FIG. 28 illustrates a block diagram 2800 that shows additional interactions with respect to treatment plans between an appliance design computational device 102 and a clinic site device 104, in accordance with certain embodiments. The process for treatment plan modification and approval is shown in FIG. 28.

FIG. 28 shows exemplary displays 2802 in a graphical user interface associated with the treatment plan review and modification application 116 at the clinic site device 104. The tentative treatment plan 2804 received from the appliance design computational device 102 is displayed. Also displayed are a sequence of images 2806 based on which the tentative treatment plan 2804 was generated by the appliance design computational device 102. The sequence of images 2806 may be processed images sent from the appliance design computational device 102 to the clinic site device 104. Thus the dental practitioner is not only displayed the tentative treatment plan 2804 but is also displayed the processed images 2806 based on which the treatment plan 2804 was generated. Therefore, the dental practitioner is in a position to evaluate the correctness of the treatment plan. It may be noted that in many cases the first treatment plan suggested by the appliance design application may be an incomplete treatment plan that may need further refinements. An indicator, such as a start approval process indicator 2808 is displayed to the dental practitioner. If the dental practitioner clicks (reference numeral 2810) on the start approval process indicator 2808, the process for approving the treatment plan is started with the dental practitioner acknowledging that the sequence of images 2806 have been viewed and the tentative treatment plan 2804 has been approved. In case the dental practitioner wishes to modify the tentative treatment plan, a modifications indicator 2810 that is displayed may be clicked.

In certain embodiments, the appliance design computational device 102 maintains a record on changes, acknowledgements, approvals, etc. in association with corresponding timestamps with respect to the treatments plans in a log file 170.

Figure 29:
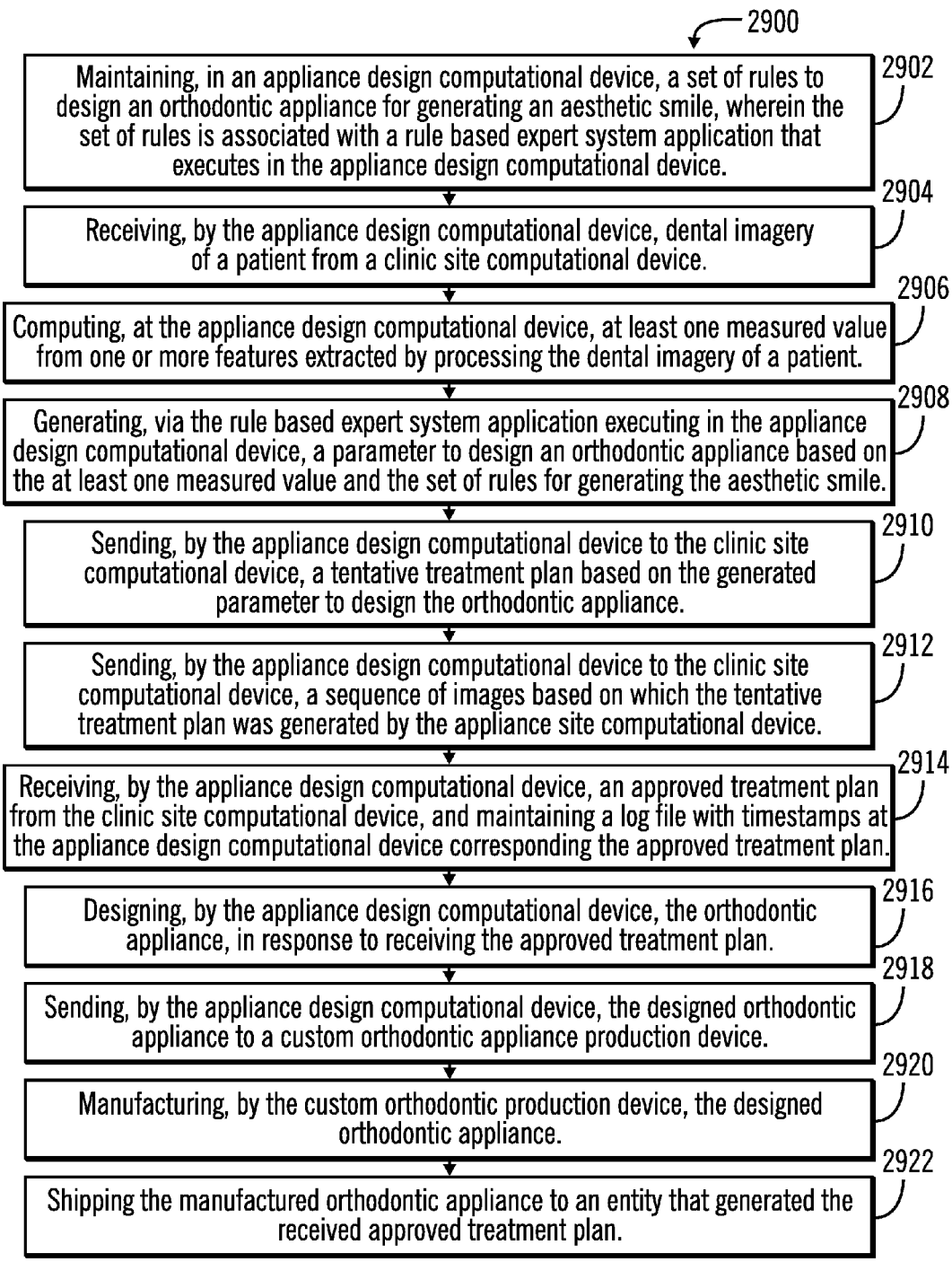
FIG. 29 illustrates a flowchart that shows certain operations performed by an appliance design computational device, in accordance with certain embodiments.

FIG. 29 illustrates a flowchart 2900 that shows certain operations 800 performed at an orthodontic appliance production site 108, in accordance with certain embodiments. Certain operations are performed by an appliance design computational device 102, wherein the appliance design application 144 and the rule based expert system application 146 execute in the appliance design computational device 102 at the orthodontic appliance production site 108. Other operations are performed by the custom orthodontic appliance production device 158.

Control starts at block 2902, in which a set of rules to design an orthodontic appliance for generating an aesthetic smile are maintained in an appliance design computational device 102, wherein the set of rules is associated with a rule based expert system application 146 that executes in the appliance design computational device 102.

Control proceeds to block 2904 in which the appliance design computational device 102 receives dental imagery 114 of a patient from a clinic site device 104 (the clinic site device 104 may also be referred to as a clinic site computational device 104). At least one measured value (e.g., inter-commissure width 1002, 1102, 2306) is computed (at block 2906) at the appliance design computational device 102, from one or more features extracted by processing dental imagery 114 of the patient, wherein the dental imagery 114 is received from a clinic site device 104. The rule based expert system application 146 that executes in the appliance design computational device 102 generates (at block 2908) a parameter (e.g. dimension 2404) to design an orthodontic appliance based on the at least one measured value and the set of rules 148 for generating the aesthetic smile.

The appliance design computational device 102 sends (at block 2910) a tentative treatment plan based on the generated parameter to design the orthodontic appliance to the clinic site device 104. The appliance design computational device 102 also sends (at block 2912) to the clinic site device 104, a sequence of images based on which the tentative treatment plan was generated by the appliance site computational device 102. The appliance design computational device 102 receives (at block 2914) an approved treatment plan from the clinic site device 104, and maintains a log file 170 with timestamps corresponding the approved treatment plan.

The appliance design computational device 102, designs (at block 2916) the orthodontic appliance, in response to receiving the approved treatment plan. The appliance design computational device 102 sends (at block 2918) the designed orthodontic appliance to a custom orthodontic appliance production device 158.

The custom orthodontic production device manufactures (at block 2920) the designed orthodontic appliance. The manufactured orthodontic appliance is addressed to an entity that generated the received approved treatment plan and is shipped (at block 2922).

Therefore, FIG. 29 shows how the appliance design computational device 102 designs an orthodontic appliance by executing a rule based expert system application 146.

In certain embodiments, the appliance design computational device 102 includes code corresponding to a rule based expert system application 146 that augments an appliance design application 144. The rule based expert system application 146 maintains the set of rules 148, wherein the set of rules 148 include rules on at least aesthetics of smile. The rule based expert system application 146 also maintains anthropomorphic measurements 150 that are computed at least from digital encodings of the dental imagery. Furthermore, the rule based expert system application 146 interacts with the appliance design application 144 to generate at least the parameter to design the orthodontic appliance based on the maintained set of rules 148 and the maintained anthropomorphic measurements 150.

Figure 30:
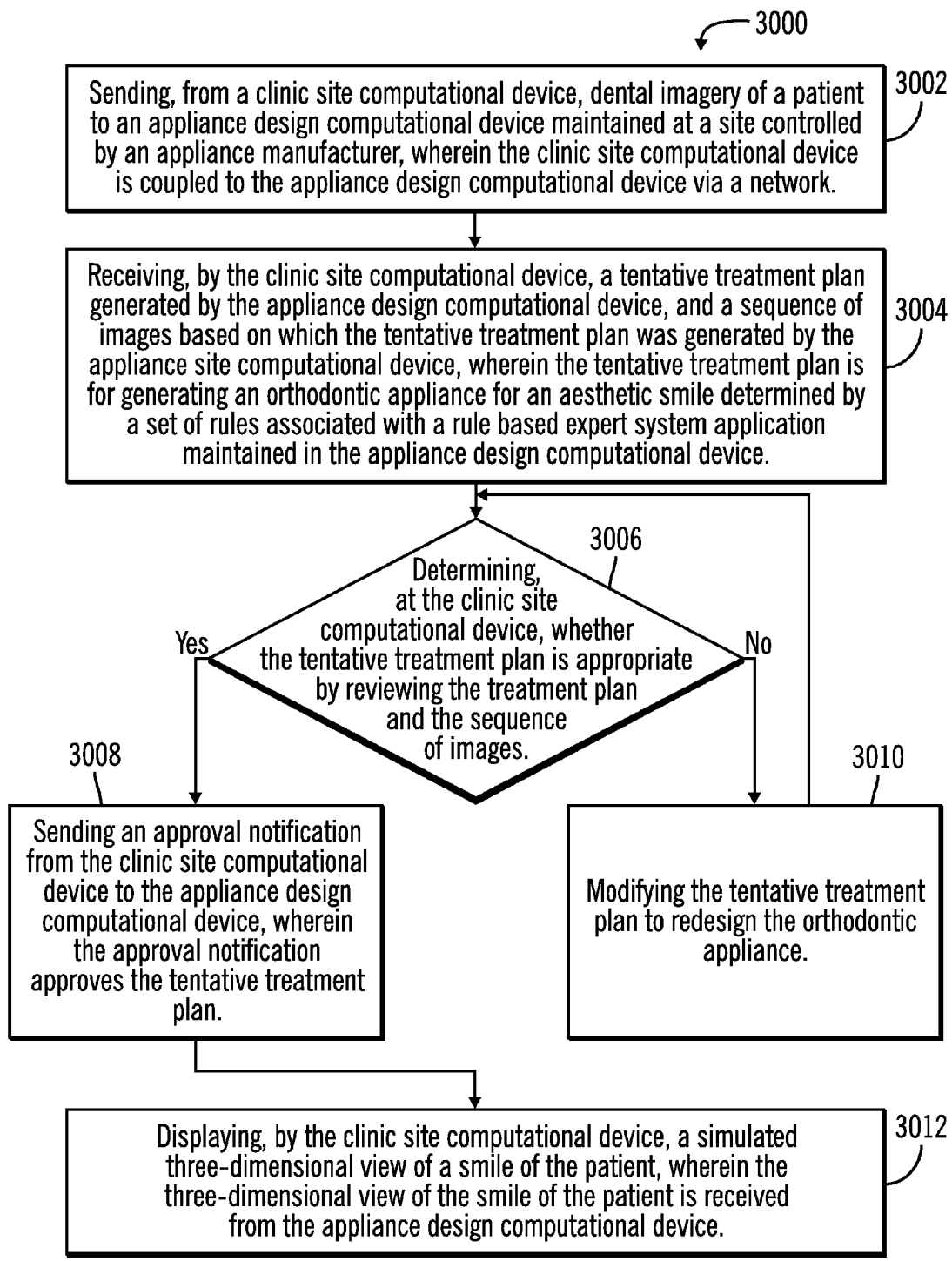
FIG. 30 illustrates a flowchart that shows certain operations performed by a clinic site device, in accordance with certain embodiments.

FIG. 30 illustrates a flowchart 3000 that shows certain operations performed by the clinic site device 104, in accordance with certain embodiments. In certain embodiments, the operations performed by the clinic site device 104 may be performed by the treatment plan review and modification application 116.

Control starts at block 3002, in which the clinic site device 104 sends dental imagery 114 of a patient to an appliance design computational device 102 maintained at a site controlled by an appliance manufacturer, wherein the clinic site device 104 is coupled to the appliance design computational device 102 via a network 106. The clinic site device 104 receives (at block 3004) a tentative treatment plan generated by the appliance design computational device 102, and a sequence of images based on which the tentative treatment plan was generated by the appliance site computational device 102, wherein the tentative treatment plan is for generating an orthodontic appliance for an aesthetic smile determined by a set of rules associated with a rule based expert system application 146 maintained in the appliance design computational device 102.

Control proceeds to block 3006, in which a determination is made at the clinic site device 104, whether the tentative treatment plan is appropriate, by reviewing the tentative treatment plan and the sequence of images. In response to determining that the tentative treatment plan is appropriate ("Yes" branch from block 3006), an approval notification is sent from the clinic site device 104 to the appliance design computational device 102, wherein the approval notification approves the tentative treatment plan. In response to determining that the tentative treatment plan is not appropriate ("No" branch from block 3006) the tentative treatment plan is modified (at block 3010) to redesign the orthodontic appliance and control returns to block 3006.

From block 3008 control proceeds to block 3012, in which the clinic site device 104 displays a simulated two-dimensional or three-dimensional view of a smile of the patient to the patient, wherein the three-dimensional view of the smile of the patient is received from the appliance design computational device 102.

Therefore, FIGS. 1-30 illustrate certain embodiments that show interactions between an appliance design computational device 102 and a clinic site device 104. An orthodontic appliance is designed based on rules and anthropomorphic measurements maintained or computed at the appliance design computational device 102. The orthodontic appliance may be designed to provide the patient with a smile in conformance with rules for incorporating smile maintained by a rule based expert system application 146 in the appliance design computational device 102.

Additional Details of Embodiments

The operations described in FIGS. 1-30 may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, infrared, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 31:
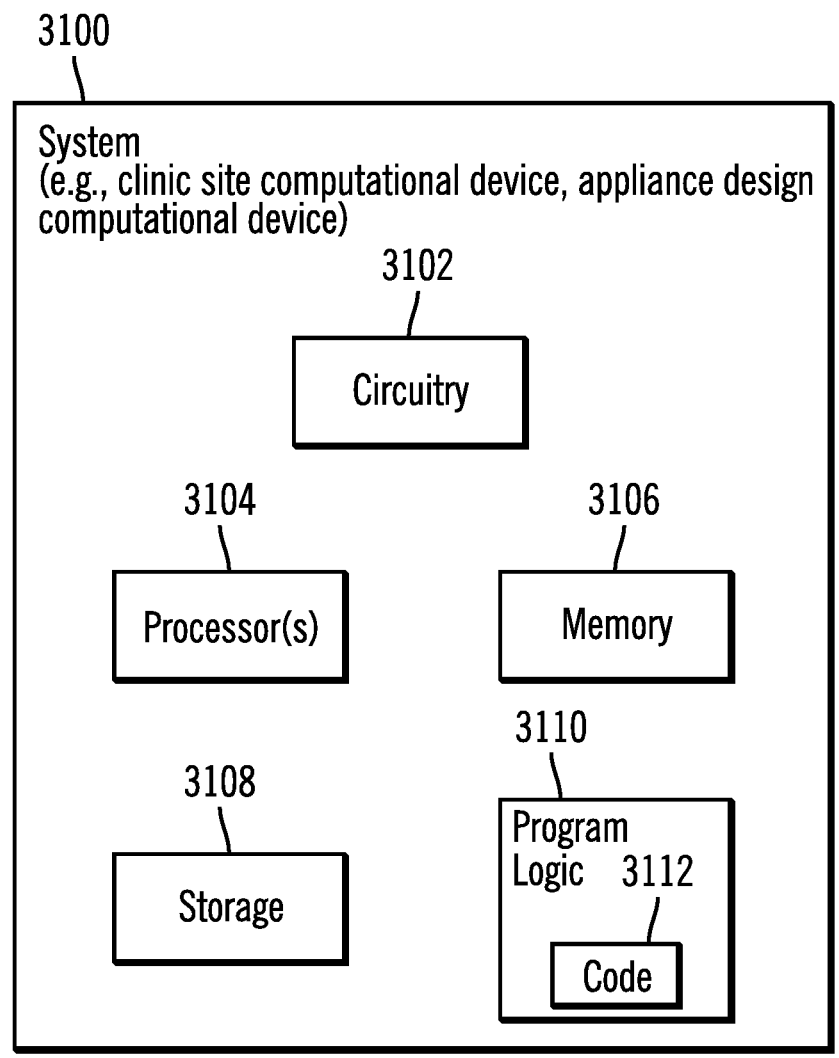
FIG. 31 illustrates a block diagram of a computational system that shows certain elements of the appliance design computational device and the clinic site device, in accordance with certain embodiments.

FIG. 31 illustrates a block diagram that shows certain elements that may be included in the appliance design computational device 102 and the clinic site device 104, in accordance with certain embodiments. The system 3100 may comprise the appliance design computational device 102 and the clinic site device 104 and may include a circuitry 3102 that may in certain embodiments include at least a processor 3104. The system 3100 may also include a memory 3106 (e.g., a volatile memory device), and storage 3108. The storage 3108 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 3108 may comprise an internal storage device, an attached storage device and/or a network accessible storage device. The system 3100 may include a program logic 3110 including code 3112 that may be loaded into the memory 3106 and executed by the processor 3104 or circuitry 3102. In certain embodiments, the program logic 3110 including code 3112 may be stored in the storage 3108. In certain other embodiments, the program logic 3110 may be implemented in the circuitry 3102. Therefore, while FIG. 31 shows the program logic 3110 separately from the other elements, the program logic 3110 may be implemented in the memory 3106 and/or the circuitry 3102.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A computer implemented method of creating an orthodontic appliance, comprising:
acquiring a set of anthropomorphic measurements of a patient into a computational device, wherein at least one anthropomorphic measurement in the set of anthropomorphic measurements is a commissure width of the patient;
maintaining, in a computational device, a set of rules to design an orthodontic appliance for generating an aesthetic smile, wherein the set of rules is associated with an application that executes in the computational device;
selecting a rule in the set of rules;
generating, via the application, a parameter to design the orthodontic appliance based on at least one anthropomorphic measurement in the set of anthropomorphic measurements and at least the selected rule in the set of rules for generating the aesthetic smile, wherein the parameter is a dimension of the orthodontic appliance, and is configured to allow the patient employing the orthodontic appliance on the patient's teeth to achieve the aesthetic smile in conformance with a selected rule, and the selected rule relates the measured commissure width to the parameter; and
manufacturing an orthodontic appliance based upon an appliance design created from the generated parameter.

2. The method of claim 1, the method further comprising:
generating a three-dimensional view of the aesthetic smile of the patient based on simulating a treatment of the patient with the designed orthodontic appliance; and
transmitting the three-dimensional view of the aesthetic smile of the patient.

3. The method of claim 2, the method further comprising:
displaying the three-dimensional view of the aesthetic smile of the patient, to the patient.

4. The method of claim 1, further comprising:
generating a tentative treatment plan based on a sequence of images;
sending the tentative treatment plan and the sequence of images;
receiving an approved treatment plan, in response to the sending of the tentative treatment plan and the sequence of images; and
maintaining a log file with timestamps corresponding the approved treatment plan.

5. The method of claim 4, further comprising:
designing the orthodontic appliance, in response to receiving the approved treatment plan; and
sending the designed orthodontic appliance to a custom orthodontic appliance production device.

6. The method of claim 5, further comprising:
manufacturing, by the custom orthodontic appliance production device, the designed orthodontic appliance; and
shipping the manufactured custom orthodontic appliance.

7. The method of claim 1, wherein:
the computational device is maintained at a site controlled by a manufacturer of the orthodontic appliance; and
a clinic site device is maintained at a site controlled by a dental practitioner.

8. The method of claim 1, wherein the set of anthropomorphic measurements is acquired from photographic imagery, digital video imagery, intra-oral scan imagery, cone beam computed tomography imagery, X-ray imagery, magnetic resonance imagery, ultrasound imagery, electron beam imagery, images of soft tissue, images of hard tissue, images of teeth of the patient, or a combination thereof.

9. The method of claim 1, wherein the selected rule provides an optimal smile to the patient in conformance with an optimization criterion associated with the selected rule.

10. The method of claim 1, wherein the computational device receives general case preferences from a dental practitioner during registration of the dental practitioner, and wherein the general case preferences include at least one of appliance preferences, torque values, and end of treatment preferences.

11. The method of claim 1, wherein the set of anthropomorphic measurements is acquired from a photograph taken at an eye level of the patient.

12. The method of claim 1, wherein the anthropomorphic measurements include commissure width, curvature of lower lip, incisor display dimension, philtrum length, crown height, gingiva display, lip incompetence, facial symmetry, or a combination thereof.

13. The method of claim 1, further comprising:
provided weightings to one or more factors, wherein the factors include a smile index, an incisor display, a commissure width, a philtrum length, a crown height, an incisor at rest characteristic, a gingiva display on smile characteristic, a lip incompetence, a facial symmetry, or a combination thereof; and
generating a composite score for the aesthetic smile using weighting of the one or more factors.

14. The method of claim 1, wherein the set of rules quantifies the aesthetic smile by using:
macro-aesthetics rules;
mini-aesthetics rules;
micro-aesthetics rules, or a combination thereof.

15. The method of claim 14, wherein the macro-aesthetics rules relate to one or more factors selected from a group consisting of:
profile;
lip fullness;
chin projection;
nasal base width;
nasofrontal angle;
vertical proportions;
intercanthal distance;
nasal projection;
pupil-midfacial distance; and
nasolabial angle.

16. The method of claim 14, wherein the mini-aesthetics rules relate to one or more factors selected from a group consisting of:
incisor display;
crowding;
smile symmetry;
transverse smile;
gingival display;
vermilion display;
smile arc;
occlusal space cant; and
buccal corridor.

17. The method of claim 14, wherein the micro-aesthetics rules relate to one or more factors selected from a group consisting of:
tooth shape;
incisor angulations;
tooth height and width relationship;
relative proportions central incisor, lateral incisor, canine, and first premolar;
tooth shade;
gingival height;
emergence profile; and
spacing.

18. The method of claim 1, wherein to generate an aesthetic smile, the orthodontic appliance is designed to perform:
changing of tooth positioning via appliance parameters to change transverse smile characteristics.

19. The method of claim 18, wherein to generate an aesthetic smile, the orthodontic appliance is further designed to perform:
correcting of flat smile via changing appliance parameters to at least extrude maxillary incisors.

20. The method of claim 19, wherein to generate an aesthetic smile, the orthodontic appliance is further designed to perform:
generation of broader smile via broader arch wires.

21. The method of claim 20, wherein to generate an aesthetic smile, the orthodontic appliance is further designed to perform:
correcting of dental crowding via expansion of arch.

22. The method of claim 21, wherein to generate an aesthetic smile, the orthodontic appliance is further designed to perform:
correcting of excessive mandibular incisor protrusion.

* * * * *